(12) United States Patent
Potyrailo et al.

(10) Patent No.: US 10,966,657 B2
(45) Date of Patent: Apr. 6, 2021

(54) SENSING SYSTEM AND METHOD

(71) Applicant: General Electric Company, Schenectady, NY (US)

(72) Inventors: Radislav Alexandrovich Potyrailo, Niskayuna, NY (US); Richard St. Pierre, Niskayuna, NY (US); Bruce Courtney Amm, Clifton Park, NY (US); Aghogho Atemu Obi, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/400,146

(22) Filed: May 1, 2019

(65) Prior Publication Data
US 2020/0345300 A1 Nov. 5, 2020

(51) Int. Cl.
*A61B 5/00* (2006.01)

(52) U.S. Cl.
CPC ............ *A61B 5/681* (2013.01); *A61B 5/0059* (2013.01); *A61B 5/7221* (2013.01); *A61B 2560/0242* (2013.01)

(58) Field of Classification Search
CPC ..... A61B 5/681; A61B 5/0059; A61B 5/7221; A61B 2560/0242
See application file for complete search history.

(56) References Cited

U.S. PATENT DOCUMENTS

| | | | |
|---|---|---|---|
| 8,403,845 | B2 | 3/2013 | Stivoric et al. |
| 9,131,892 | B2 | 9/2015 | Markel |
| 9,526,452 | B2 | 12/2016 | Markel |
| 9,750,462 | B2 | 9/2017 | Leboeuf et al. |

(Continued)

FOREIGN PATENT DOCUMENTS

WO 2016110804 A1 7/2016

OTHER PUBLICATIONS

Ermes et al., "Detection of Daily Activities and Sports With Wearable Sensors in Controlled and Uncontrolled Conditions", IEEE Transactions on Information Technology in Biomedicine, vol. 12, Issue 1, pp. 20-26, Jan. 2008.

(Continued)

*Primary Examiner* — Ziaul Karim
(74) *Attorney, Agent, or Firm* — Mary D. Lawlor; The Small Patent Law Group LLC

(57) ABSTRACT

A sensor system includes a first sensor to detect environmental conditions of an environment in operational contact with a subject, a second sensor to detect physiological parameters of the subject in operational contact with an asset, and a control unit comprising one or more processors communicatively coupled with the first sensor and the second sensor. The processors receive a first signal from the first sensor indicative of the environmental conditions, and receive a second signal from the second sensor indicative of the physiological parameters of the subject, and determine a relation between the environmental conditions and the physiological parameters based on the first signal and the second signal. The processors determine a responsive action of the asset based on the first signal indicative of the environmental conditions of the environment or the second signal indicative of the physiological parameters of the subject in operational contact with the asset.

30 Claims, 14 Drawing Sheets

(56) References Cited

U.S. PATENT DOCUMENTS

| | | | |
|---|---|---|---|
| 9,950,236 B1* | 4/2018 | Jooste | A63B 71/06 |
| 10,105,097 B2 | 10/2018 | Markel | |
| 2013/0267789 A1 | 10/2013 | Stivoric et al. | |
| 2014/0228649 A1* | 8/2014 | Rayner | A61B 5/6898 600/301 |
| 2016/0014129 A1* | 1/2016 | Park | A61B 5/681 726/1 |
| 2016/0084869 A1* | 3/2016 | Yuen | B60B 33/00 73/510 |
| 2017/0365152 A1 | 12/2017 | Parra et al. | |
| 2018/0050171 A1* | 2/2018 | Tabert | A61B 5/7415 |
| 2018/0151047 A1 | 5/2018 | Brunner et al. | |
| 2018/0220905 A1 | 8/2018 | Leboeuf et al. | |
| 2018/0271442 A1 | 9/2018 | Dupuy | |
| 2018/0322950 A1* | 11/2018 | Cronin | A61B 5/0008 |
| 2018/0325385 A1 | 11/2018 | Deterding et al. | |
| 2020/0013501 A1* | 1/2020 | Page | G08B 21/24 |

OTHER PUBLICATIONS

Pantelopoulos et al., "A Survey on Wearable Sensor-Based Systems for Health Monitoring and Prognosis", IEEE Transactions on Systems, Man, and Cybernetics, Part C (Applications and Reviews), vol. 40, Issue 1, pp. 1-12, Jan. 2010.

Misra et al., "Flexible Technologies for Self-Powered Wearable Health and Environmental Sensing", Proceedings of the IEEE, vol. 103, Issue 04, pp. 665-681, Apr. 2015.

Douglas et al., "National Athletic Trainers' Association Position Statement: Exertional Heat Illnesses", Journal of Athletic Training, vol. 50, Issue 9, pp. 986-1000, Sep. 2015.

Dieffenderfer et al., "Low-Power Wearable Systems for Continuous Monitoring of Environment and Health for Chronic Respiratory Disease", IEEE Journal of Biomedical and Health Informatics, vol. 50, Issue 5, pp. 1251-1264, Sep. 2016.

Wells et al., "Reactive indoor air chemistry and health—A workshop summary", International Journal of Hygiene and Environmental Health, vol. 220, Issue 8, pp. 1222-1229, Nov. 2017.

Ibukun et al., "Wearable technology for personalized construction safety monitoring and trending: Review of applicable devices", Automation in Construction, vol. 85, pp. 96-106, Jan. 2018.

Baichen et al., "A Wearable IoT Aldehyde Sensor for Pediatric Asthma Research and Management", arXiv, Nov. 18, 2018.

Mead, M. I., et al "The use of electrochemical sensors for monitoring urban air quality in low-cost, high-density networks", Atmospheric Environment 2013, 70, 186-203.

Kumar, P., "The rise of low-cost sensing for managing air pollution in cities", Environment International 2015, 75, 199-205.

Schneider, P., et al, "Mapping urban air quality in near real-time using observations from low-cost sensors and model information", Environment international 2017, 106, 234-247.

Spinelle, L., et al, "Field calibration of a cluster of low-cost available sensors for air quality monitoring Part A: Ozone and nitrogen dioxide", Sens. Actuators, B 2015, 215, 249-257.

Spinelle, L., et al, "Field calibration of a cluster of low-cost commercially available sensors for air quality monitoring. Part B", NO, CO and CO2, Sens. Actuators, B 2017, 238, 706-715.

Van den Bossche, M., et al, "Potential of a low-cost gas sensor for atmospheric methane monitoring, Sensors and Actuators B", Chemical 2017, 238, 501-509.

Lewis, A., et al, "Validate personal air-pollution sensors", Nature 2016, 535, 29-31.

Potyrailo, R. A., "Multivariable sensors for ubiquitous monitoring of gases in the era of Internet of Things and Industrial Internet", Chem. Rev. 2016, 116, 11877-11923.

Potyrailo, R. A., et al, "A. Materials and Transducers Toward Selective Wireless Gas Sensing", Chem. Rev. 2011, 111, 7315-7354.

Potyrailo, R. A., "Toward high value sensing: monolayer-protected metal nanoparticles in multivariable chemical and vapor sensors", Chem. Soc. Rev. 2017, 46, 5311-5346.

Van Hoof, C., "Fitness Wearables Lack Accuracy", EE Times 2014, http://www.eetimes.com/author.asp?section_id=36&doc_id= 1321976.

Metz, R., "The Struggle for Accurate Measurements on Your Wrist", MIT Techn. Rev. 2015, https://www.technologyreview.com/s/538416/ the-struggle-for-accurate-measurements-on-your-wrist/.

Richmond, S., "The real world wrist-based heart rate monitor test: Are they accurate enough?", Wareable 2015, http://www.wareable. com/fitness-trackers/heart-rate-monitor-accurate-comparison-wrist.

Case, M. A., et al, "Accuracy of smartphone applications and wearable devices for tracking physical activity data", JAMA 2015, 313, 625-626.

Evenson, K. R., et al, "Systematic review of the validity and reliability of consumer-wearable activity trackers", Int. J. Behav. Nutr. Phys. Act. 2015, 12, 12:159.

Gibney, E., "The body electric", Nature 2015, 528, (7580), 26-28.

Savage, N., "Mobile data: Made to measure", Nature 2015, 527, (7576), S12-S13.

Zhu, Y., "Electrocardiogram of a Silver Nanowire Based Dry Electrode: Quantitative Comparison With the Standard Ag/AgCl Gel Electrode", IEEE, Feb. 5, 2019, pp. 1-12.

Ford, J., "Silver nanowire wearable sensors match hospital 'wet electrode' accuracy", The Engineer 2015, http://www.theengineer. co.uk/silver-nanowire-wearable-sensors-match-hospital-wet-electrode-accuracy/.

Del Din, S., "Free-living monitoring of Parkinson's disease: Lessons from the field", Mov. Disord. 2016, 31, (9), 1293-1313.

Knight, W., "How to make a smartphone detect anemia with FDA-approved accuracy", MIT Techn. Rev. 2016, https://www. technologyreview.com/s/602248/how-to-make-a-smartphone-detect-anemia/.

Binkley, H. M., et al, "National Athletic Trainers' Association position statement: exertional heat illnesses", Journal of Athletic Training 2002, 37, (3), 329.

Wells, J., et al, "Reactive indoor air chemistry and health—A workshop summary", International journal of hygiene and environmental health 2017.

Awolusi, I., "Wearable technology for personalized construction safety monitoring and trending: Review of applicable devices", Automation in Construction 2018, 85, 96-106.

Yang, Y., et al, "Wearable and flexible electronics for continuous molecular monitoring", Chemical Society Reviews 2018.

* cited by examiner

SENSING SYSTEM AND METHOD

FIELD

One or more embodiments are disclosed that relate to systems and methods for sensing environmental conditions and physiological parameters.

BACKGROUND

Wearable gas sensors are intended to track changes of environmental gases in real time. At present, the accepted limitations of known wearable gas sensors include poor selectivity that can lead to false alarms about the presence of gases of interest in complex real-world environments. Such gases may be masked by other gases, which can lead to interferences in determinations. Wearable physiological sensors experience performance improvements based on design principles that allow these sensors to compete with the performance of standard hospital and wet-electrode-based instruments.

While the number of wearable sensors for diverse physiological parameters is expanding, these sensors do not have the ability to accurately detect environmental parameters. While successful sensors include detection of ambient temperatures, accurate analysis of gases and other environmental parameters is problematic and cannot be accomplished accurately with known wearable sensor technology. Because of the lack of needed accuracy, existing sensors are problematic to utilize for control of environmental conditions and/or assets that are operated by subjects.

BRIEF DESCRIPTION

In one or more embodiments, a sensor system includes a first sensor configured to detect one or more environmental conditions of an environment in operational contact with a subject, a second sensor configured to detect one or more physiological parameters of the subject in operational contact with an asset, and a control unit comprising one or more processors communicatively coupled with the first sensor and the second sensor. The one or more processors are configured to receive a first signal from the first sensor indicative of the one or more environmental conditions, and receive a second signal from the second sensor indicative of the one or more physiological parameters of the subject. The one or more processors are configured to determine a relation between the one or more environmental conditions from the first sensor and the one or more physiological parameters from the second sensor based on the first signal and the second signal. The one or more processors are configured to determine a responsive action of the asset based on one or more of the first signal indicative of the one or more environmental conditions of the environment in operational contact with the subject or the second signal indicative of the one or more physiological parameters of the subject in operational contact with the asset.

In one or more embodiments, a sensor system includes a first sensor configured to detect one or more environmental conditions of an environment in operational contact with a subject, a second sensor configured to detect one or more physiological parameters of the subject in operational contact with an asset, and a control unit having one or more processors communicatively coupled with the first sensor and the second sensor. The one or more processors are configured to receive a first signal from the first sensor indicative of the one or more environmental conditions, and receive a second signal from the second sensor indicative of the one or more physiological parameters of the subject. The one or more processors are configured to determine a relation between the one or more environmental conditions from the first sensor and the one or more physiological parameters from the second sensor based on the first signal and the second signal. The one or more processors are configured to determine a responsive action of the subject based on the one or more of the first signal indicative of the one or more environmental conditions of the environment in operational contact with the subject or the second signal indicative of the one or more physiological parameters of the subject in operational contact with the asset. The one or more processors are configured to determine a responsive action of the asset based on the second signal indicative of the one or more physiological parameters of the subject.

In one or more embodiments, a method includes detecting one or more environmental conditions of an environment in operational contact with a subject with a first sensor of a sensor system, and detecting one or more physiological parameters of the subject in operational contact with an asset with a second sensor of the sensor system. A first signal is received from the first sensor indicative of the one or more environmental conditions of the environment in operational contact with the subject. A second signal is received from the second sensor indicative of the one or more physiological parameters of the subject. A relation is determined between the one or more environmental conditions from the first sensor and the one or more physiological parameters from the second sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset is determined based on the second signal indicative of the one or more physiological parameters of the subject.

In one or more embodiments, a method includes detecting one or more environmental conditions of an environment in operational contact with a subject with an environmental sensor of a sensor system, and detecting one or more physiological parameters of the subject in operational contact with an asset with a physiological sensor of the sensor system. A first signal is received from the environmental sensor indicative of the one or more environmental conditions of the environment in operational contact with the subject. A second signal is received from the physiological sensor indicative of the one or more physiological parameters of the subject. A relation is determined between the one or more environmental conditions from the environmental sensor and the one or more physiological parameters from the physiological sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset of the subject is determined based on the second signal indicative of the one or more physiological parameters of the subject. A notification is transmitted to one or more of the subject or one or more users of the sensor system based on one or more of the environmental signal or the physiological signal exceeding a designated threshold.

In one or more embodiments, a method includes detecting one or more environmental conditions of an environment in operational contact with a subject with a first sensor of a sensor system, detecting one or more physiological parameters of the subject in operational contact with an asset with a second sensor of the sensor system, and communicatively coupling the first sensor and the second sensor with a control unit. A first signal is received from the first sensor indicative of the one or more environmental conditions of the environment in operational contact with the subject. A second signal is received from the second sensor indicative of the one or more physiological parameters of the subject. A relation is determined between the one or more environmental conditions from the first sensor and the one or more physiological parameters from the second sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset is determined based on the second signal indicative of the one or more physiological parameters of the subject.

DETAILED DESCRIPTION

Figure 1:
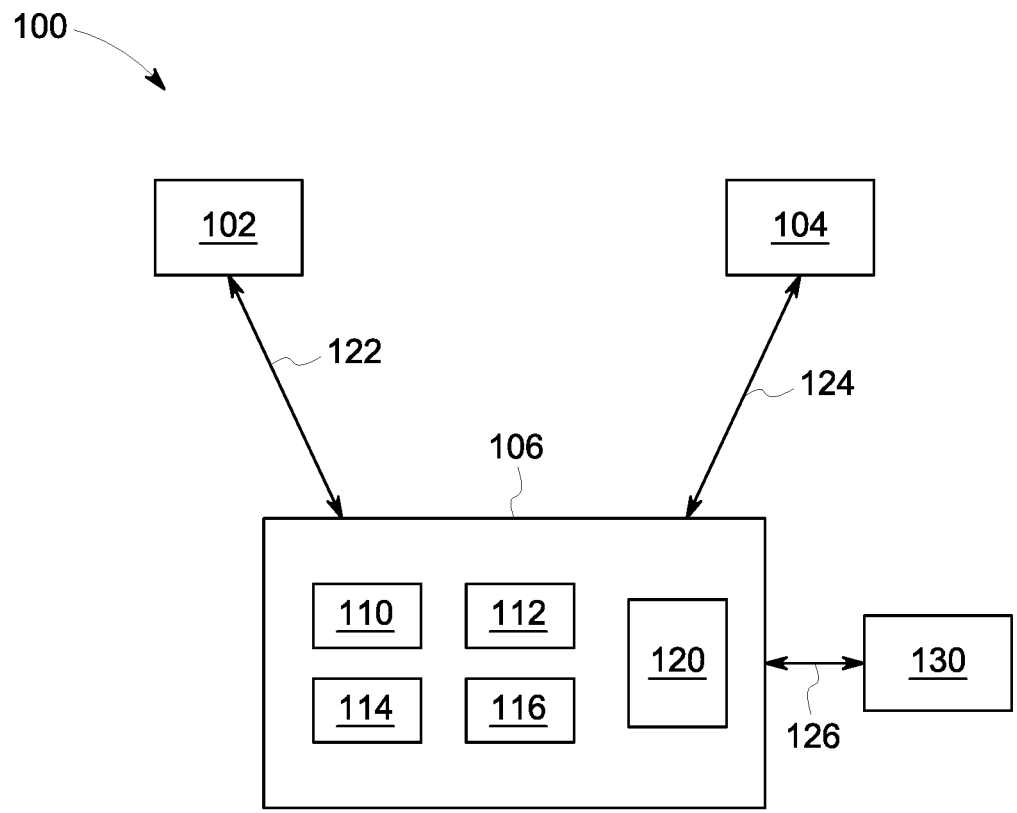
FIG. 1 illustrates one embodiment of a sensor system in accordance with one embodiment.

One or more embodiments of the inventive subject matter described herein provide for sensing systems and methods that detect environmental conditions in operational contact with a subject and physiological parameters of the subject in the operational contact with an asset, and that relate to responsive actions of the subject in the operational contact with the environment and that relate to responsive actions of the asset. The systems and methods determine a relation between the environmental conditions and the physiological parameters. An excitation assembly operates the environmental and physiological sensors. One or more processors of a control unit receives and processes data from the environmental sensor and the physiological sensor. The one or more processors further determine a relation between the data provided via the environmental and physiological sensors. The environmental sensor and the physiological sensor may be held within a common wearable or non-wearable transferrable object, such as a frame of military or industrial eyeglasses, a wearable pulse oximeter, a safety vest or harness, an article of clothing, a mobile device (e.g., a cellular phone, a tablet, or the like), or the like. Optionally, the environmental sensor and the physiological sensor may be held in separate and distinct wearable or non-wearable transferrable objects.

The excitation assembly applies a first electrical, optical, mechanical, thermal, and/or magnetic stimuli to a sensing element of an environmental sensor to detect the one or more environmental conditions, and applies a second electrical, optical, mechanical, thermal, and/or magnetic stimuli to a physiological sensing element of a physiological sensor to detect the one or more physiological parameters. The first and second stimuli may be applied via an excitation assembly. Nonlimiting examples of sensor-excitation include steady-state excitation, periodic excitation, gated excitation, pulsed excitation, and variable duty cycle excitation.

The one or more processors of the control unit receive an environmental signal from the environmental sensor indicative of the environmental conditions. Nonlimiting examples of the environmental conditions measured and/or detected by the environmental sensor can include gas, particle matter contaminants (PM), ultraviolet radiation exposure (UV), ambient temperature, ambient pressure, ambient relative humidity, and sensor acceleration.

The one or more processors also receive a physiological signal from the physiological sensor indicative of the physiological parameter. Nonlimiting examples of the physiological parameters measured and/or detected by the physiological sensor can include, but are not limited to, skin temperature, core body temperature, skin conductivity, blood pressure, systolic blood pressure variability, blood glucose, respiration rate, respiration rate variability, oxygen saturation, oxygen saturation variability, heart rate, heart rate variability, heart sounds, body movements (e.g., abduction, adduction, extension, flexion, rotation, and circumduction), muscle analysis, gate and gait analysis, brain activity, or the like. These and other measured physiological parameters are related to neural, respiratory, circulatory, cardiac, hemodynamic, and/or metabolic and other physiological functions of the subject.

As a result, or responsive to the correlation that is determined between the environmental conditions and the physiological parameters, a subject can perform some actions or activities. Such actions by the subject can include external actions (e.g., apply physical activity to operate a device, apply physical activity to move body or parts of the body, or the like) or internal actions (e.g., to induce a different state or different activity, such as taking medication, to move, to sleep, to eat and/or drink, to see a doctor, or the like). Optionally, actions can be taken by an environment or asset in relation to the subject. Such actions can be asset control (e.g., put into autopilot, or the like). Optionally, the outcomes of operation of the sensor system can include diagnostics, prognostics, observing, reporting, controlling, and other outcomes.

At least one technical effect of the various embodiments herein includes a sensor system that allows an accurate determination of environmental gases and to correlate the detected gases with physiological responses of a subject. As an additional technical effect, the multivariable environmental and physiological sensors provide plural outputs to detect diverse properties of an ambient environment. The multivariable sensor system design includes the environmental and physiological sensing capabilities. As an additional technical effect, the sensor system and method embodiments herein use common sensor-excitation and signal-processing units to operate the environmental sensor and the physiological sensor, and to determine the correlation between the environmental conditions detected by the environmental sensor and the physiological parameters detected by the physiological sensor.

FIG. 1 illustrates one embodiment of a sensor system 100. The system 100 includes an environmental sensor 102 and a physiological sensor 104. The environmental sensor 102 can sense or detect one or more environmental conditions in operational contact with a subject. The physiological sensor 104 can sense or detect one or more physiological parameters of a subject of the physiological sensor 104. The subject may be a human subject, an animal subject such as a mammal, a reptile, a bird, a fish, an amphibian, a plant subject, or the like. For example, the human subject may be a pilot, a soldier, a firefighter, an industrial worker, an athlete, a traveler, a baby or child, a hospital patient, a disabled person, an elderly person, or the like. In another embodiment, the subject may be a robot or robotic subject. In one or more embodiments, the physiological sensor 104 can sense or detect physiological parameters of the subject in operational contact with an asset. Suitable environmental and physiological sensors 102, 104 may include single use or multi-use sensors. A suitable multi-use sensor may be a re-usable sensor that may be used during the lifetime of a system in which it may be incorporated into. In one embodiment, the sensor may be a single use sensor that may be used during all or part of a reaction or process.

The environmental sensor 102 may detect characteristics or properties of a fluid. The fluid may be a gas, a liquid, or a gas-liquid mixture containing one or more analyte gases therein. In another embodiment, the fluid may be a gas or water, de-icing fluid, decreasing fluid, aqueous fluid, non-aqueous fluid, organic solvent, inorganic solvent, dust pollen, powder, aerosol, mist, fog, smoke, or fuel, such as a hydrocarbon-based fuel. One example of the fluid is natural gas that is supplied to a powered system (e.g., a vehicle, or a stationary generator set) for consumption. Other examples of such a fluid can include gasoline, diesel fuel, jet fuel or kerosene, bio-fuels, petrodiesel-biodiesel fuel blends, natural gas (liquid or compressed), and fuel oils. Another example of the fluid is indoor or outdoor ambient air. Another example of the fluid is ambient air with relatively small concentrations of hydrocarbons and/or other pollutants. Another example of the fluid is at least one gas dissolved in an industrial liquid such as transformer oil, bioprocess media, fermentation media, wastewater, and any other. Another example of the fluid is the at least one gas dissolved in a consumer liquid such as milk, non-alcoholic beverages, alcoholic beverages, cosmetics, and any other. Another example of the fluid is at least one gas dissolved in a body liquid such as blood, sweat, tears, saliva, urine, and any other. Another example of the fluid is breathable air of a cabin, cockpit, a safety gas mask, confined space, breathing apparatus, or the like. Another example of the fluid is breathable air of a life system. Another example of the fluid is water, drinking water, washing water, bathing water, swimming water, lake water, river water, sea water, ocean water, or the like.

The environmental sensor 102 may detect characteristics or properties of the fluid via a resonant or non-resonant impedance spectral response. One or more of the inductor-capacitor-resistor resonant circuits (LCR resonators) may measure the resonant impedance spectral response of the sensor. A non-resonant impedance spectral response is measured when the circuit does not contain an inductor. The resonant or non-resonant impedance spectrum of the environmental sensor 102 in proximity to the fluid varies based on sample composition and/or components and/or temperature. The measured resonant or non-resonant impedance values Z' (which may be the real part of resonant impedance, Zre) and Z" (which may be the imaginary part of resonant impedance, Zim) reflect the response of the environmental sensor 102 to the fluid.

Other embodiments of the inventive subject matter described herein include other designs of sensors besides resonant and non-resonant impedance sensors. Other sensors can be capacitor sensors, electro-mechanical resonator sensors (e.g., tuning forks, cantilever sensors, acoustic device sensors), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors. The sensor may generate electrical or optical stimuli in response to measured fluid.

The environmental sensor 102 and the physiological sensor 104 are communicatively coupled with a control unit 106. A bi-directional communication link 122 couples the environmental sensor 102 and the control unit 106, and a bi-directional communication link 124 couples the physiological sensor 104 and the control unit 106. Data from each of the environmental sensor 102 and the physiological sensor 104 may be acquired by data acquisition circuitry 116 of the control unit 106. The control unit 106 can include data processing circuitry, where additional processing and analysis may be performed. The control unit 106 may include one or more wireless or wired components, and may also communicate with the other components of the system 100. Suitable communication models include wireless or wired. At least one suitable wireless model includes radio frequency devices, such as radio frequency identification (RFID) wireless communications. Other wireless communication modalities may be used based on application specific parameters. Nonlimiting examples include Bluetooth, Wi-Fi, 3G, 4G, 5G, and others. For example, where there may be electromagnetic field (EMF) interference, certain modalities may work where others may not. The data acquisition circuitry 116, optionally, can be disposed within one or both of the sensors 102, 104. For example, one or both of the sensors 102, 104 may include circuits or circuitry that allow the sensors 102, 104 to acquire data, that may be analyzed, computed, or the like, and communicated or transmitted to the control unit 106.

The data acquisition circuitry 116 may be in the form of a sensor reader, which may be configured to communicate wirelessly or wired with the sensors 102, 104. For example, the sensor reader may be a battery-operated device and/or may be powered using energy available from the main control system or by using harvesting of energy from ambient sources (light, vibration, heat, or electromagnetic energy). The data acquisition circuitry is an impedance analyzer that may provide scanning capability to measure sensor impedance responses across a predetermined frequency range, for example from 0.001 Hz to 10 GHz, from 0.1 Hz to 1 GHz, from 1 Hz to 100 MHZ, from 10 Hz to 10 MHz, or from 1000 Hz to 100 kHz. An impedance analyzer may provide capability to measure sensor impedance at discrete predetermined frequencies, for example at 1 Hz, 10 Hz, 100 Hz, 1 kHz, 10 kHz, 100 kHz, 1 MHz, 10 MHz, or 100 MHz. The data acquisition circuitry may be circuitry to collect data from capacitor sensors, electro-mechanical resonator sensors (e.g., tuning forks, cantilever sensors, acoustic device sensors, or the like), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors.

Additionally, the data acquisition circuitry may receive data from each of the sensors 102, 104. The data may be stored in short term and/or long-term memory storage devices 112, such as archiving communication systems, which may be located within or remote from the system and/or reconstructed and displayed for an operator, such as at the operator workstation, via an input/output device 114. The sensors 102, 104 may be positioned on the subject, carried by the subject, attached to the subject, attached to a garment of the subject, be a part of the garment of the subject, be integrated into the garment of the subject, be the garment itself of the subject, attached to a personal protective equipment of the subject (e.g., safety helmet, glasses, hearing device, or the like), be an integrated part of a personal protective equipment of the subject, or the like. The sensors 102, 104 may be implanted into the subject, swallowed by the subject, or digested by the subject. The sensors 102, 104 may be positioned on, in, in a pre-determined proximity to, or the like, industrial assets such as, for example, oil fluid reservoirs, associated piping components, connectors, flow-through components, and any other relevant industrial or process components.

The components or a system of components may be an asset. Nonlimiting examples of assets include an airplane, locomotive, truck, passenger car, a home appliance, a sport equipment asset, a military system, or the like. An asset is in operational contact with the subject or similarly, the subject is in operational contact with the asset. The sensor 102 is in operational contact with the environment, and the sensor 104 is in operational contact with the subject and the subject is in operational contact with the asset.

The subject may be in operational contact with the asset when the subject controls the asset with at least one level of control, when the asset provides feedback to the subject, or the like. An example of one level of control includes driving a passenger vehicle by a subject using a stick-shift clutch in a manual driving mode of the vehicle. Another example of more than one level of control includes flying an airplane, for example by a subject using a manual and/or an auto-pilot mode. The subject may be in operational contact with the asset when the asset controls the subject. For example, an asset can be an automatic set of gates that controls the travel path of the subject to pass different open gates and to avoid the closed gates along the travel path.

The environmental sensor 102 is in operational contact with the environment by immersing the sensor 102 in the fluid, placing the sensor in a headspace of the fluid, or by any alternative method. When the sensor 102 is in operational contact with the fluid, chemical and biological moieties in the fluid interact with the sensor 102 and produce a predictable multivariable sensor response. Alternatively, responsive to the sensor 102 being in operational contact with the fluid, chemical and biological moieties in the fluid can interact with the sensor 102 and produce a predictable univariable sensor response. The physical properties of the fluid can also be measured with the sensor 102. Nonlimiting examples of fluid physical properties include temperature, color, density, viscosity, scatter, refractive index, dielectric permittivity, or polarity. The operational contact may be achieved by direct immersion of the sensor 102 into the fluid, when the sensor is wetted by the fluid, or through a gas-permeable or ion-permeable membrane that may allow analytes in the fluid to transport through the membrane of the sensor while the fluid is not wetting the sensor 102, or by placing the sensor 102 in the headspace. The operational contact may also be achieved by placing the sensor 102 in a gas phase sample, wherein the gas phase sample is one or more of ambient air, cabin air, confined space air, exhaled air, inhaled air, gas mask air, gas breathing apparatus air, underground mine air, tunnel air, industrial site air, indoors and/or outdoors air, industrial and/or urban air, clean air, polluted air, or any other air intended for breathing or application by the asset.

The physiological sensor 104 is in operational contact with the subject, where the operational contact allows detection of a desired physiological parameter or plural different physiological parameters with the sensor 104. The sensor 104 can be directly touching the subject, for example, a smartwatch or alternative device with a physiological sensor touching the skin of the subject. The sensor 104 may be directly fully or partially implanted or embedded into the subject, for example, a glucose sensor implanted within the subject. The sensor 104 may be directly ingested or swallowed by the subject, for example, a swallowed dissolved gas sensor, a swallowed pressure sensor, or the like. The sensor 104 may be in proximity to the subject, and may not be in contact with the subject, for example in a cabin or a cockpit for monitoring the operator and/or driver of the vehicle to detect pilot fatigue, or the like. The sensor 104 may be a video camera, a radar, or another type of sensor positioned proximate the subject without physically contacting the subject. For example, the sensor 104 may be positioned less than 0.1 millimeter (mm) away from the subject, between 0.1 mm to about 1.0 meter (m) from the subject, between about 1.0 m to about 10.0 m from the subject, or the like. Optionally, the sensor 104 may be disposed further away or closer to the subject without contacting the subject. The sensor 104 can be in stand-off position to the subject, for example on a manufacturing floor, in an airport terminal, airborne on a drone or an airplane, an industrial site, an urban site, a rural site, a recreational site, or the like. The sensor 104 may be a multi-spectral camera, a video camera, a thermal camera, a radar, or another type of sensor positions about 1 m to about 10 km from the subject without physical contact with the subject.

In one or more embodiments, the sensor 104 that is in proximity to the subject or in a stand-off position to the subject, can be designed to provide information from one subject, or independent information from plural different subjects. For example, a sensor in a cabin of a car can provide the information about pulse rate and/or other vital signs of all passengers and a driver inside the cabin of the car. Optionally, a sensor in a stand-off position to the subject can provide the information about pulse rate and other vital signs of one air traveler in an airport, or more than one air traveler in an airport based on the design principles of the stand-off sensor.

The response of at least one sensor 104 can promote at least one or all responsive actions, such as display of type of the changed parameter of the subject or asset, level of change of the parameter, an alarm, remote data transfer, guidance of the subject to change physical activity, guidance of the subject to change physical locations, guidance of the subject to change environmental conditions around, proximate to, or in operational contact with the subject, ventilation of the area that contains the subject, evacuation of the subject, change of a control state of the asset in operational contact with the subject, change of a maintenance schedule of the asset that is in operational contact with the subject, or the like.

The data acquisition circuitry 116 may include one or more processors for analyzing the data received from the sensors 102, 104. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as the memory device 112. The memory device 112 may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

In addition to receiving and displaying data, the control unit 106 may control the above-described operations and functions of the system 100. The control unit 106 may include one or more processor-based components, such as general purpose or application-specific computers or processors 110. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the control unit 106 or by associated components of the system 100.

Alternatively, the programs and routines may be stored on a computer accessible storage and/or memory remote from the control unit 106 but accessible by network and/or communication interfaces present on the control unit 106. The control unit 106 may also comprise various input/output (I/O) interfaces or devices 114, as well as various network or communication interfaces. The various I/O devices 114 may allow communication with user interface devices, such as a display, keyboard, electronic mouse, printer, or the like, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

In one or more embodiments, the control unit 106 may be disposed in a common room, space, geographical area, or the like as the environmental sensor 102 and/or the physiological sensor 104. For example, the control unit 106 may be separated from the sensors 102, 104 by less than 1 foot, less than 10 ft, less than 50 ft, or the like. In alternative embodiments, the control unit 106 may be disposed in one room of a building and one or more of the sensors 102, 104 may be disposed in a different room of a building. Optionally, the control unit 106 may be disposed in one geographical area, and one or more of the sensors 102, 104 may be disposed in a different geographical area separated from the first geographical area by plural feet, miles, kilometers, or the like.

Figure 2:
FIG. 2 illustrates an environmental sensor in accordance with one embodiment.

FIG. 2 illustrates the environmental sensor 102 in accordance with one embodiment. The environmental sensor 102 may be a multivariable gas sensor, or may optionally represent another version of the sensors or sensing systems described herein. In one or more embodiments, the environmental sensor 102 includes an environmental sensing element 202 having a substrate 204, such as a dielectric material, with a sensing film or environmental sensing material 208 coupled to the substrate 204. The environmental sensing material 208 is exposed to, in contact with, in indirect contact with, or the like, at least one analyte gas. One or several heating elements (not shown), such as high resistance bodies, may be optionally coupled with a different side of the substrate 204 than the sensing material 208. The heating elements can receive electric current from a heater controller (not shown), which can represent hardware circuitry that conducts the heater current or voltage to the heating elements to heat the substrate 204 and to heat the environmental sensing material 208 that is coupled to a different side of the substrate 204. For example, in one or more embodiments of the inventive subject matter described herein, the environmental sensing material 208 utilizes a metal oxide sensing film. The environmental sensing material 208 can include one or more materials deposited onto the substrate 204 to perform a function of predictably and reproducibly affecting the impedance sensor response upon interaction with the environment. For example, a metal oxide such as $SnO_2$ may be deposited as the environmental sensing material 208.

Sensing electrodes 210, 212 are coupled with or disposed in the environmental sensing material 208 and are connected with the substrate 204 in the illustrated embodiment. The sensing electrodes 210, 212 are conductive bodies that are conductively coupled with an excitation assembly 120 of the control unit 106 (shown in FIG. 1). The excitation assembly 120 can include one or more processors that include one or more microprocessors, field programmable gate arrays, and/or integrated circuits.

In an embodiment, the environmental sensor 102 can be designed to operate based on electrical, optical, mechanical, thermal, and/or magnetic transducer principles. Depending on the operation principles, the environment in the operational contact with the sensor predictably affects electrical, optical, mechanical, thermal, and/or magnetic properties of the sensing structure and a relation is established between an amount of an environmental change and the strength of a signal produced by the sensor 102. General transduction principles can also include different variations. As a result, designs of sensors include resonant and non-resonant impedance sensors, capacitor sensors, electro-mechanical resonator sensors (e.g., tuning forks, cantilever sensors, acoustic device sensors, or the like), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, single-output sensors, or the like. Additionally or alternatively, the environmental sensor 102 can be based on the sensing materials that predictably change one or more detected properties as correlated with the amount of the environmental change of the detected fluid, and can be based on direct detection of one or more properties of the detected fluid.

Figure 3:
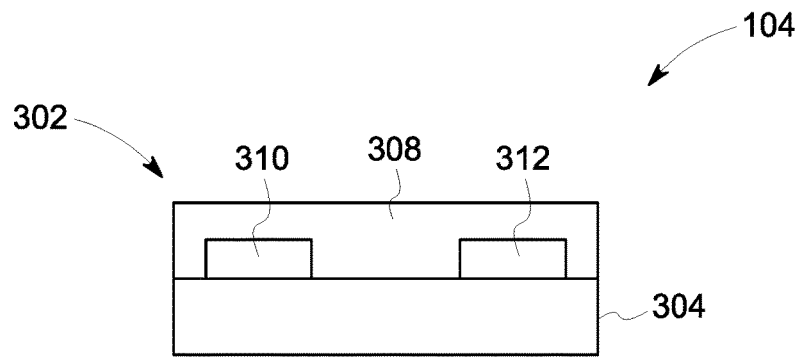
FIG. 3 illustrates a physiological sensor in accordance with one embodiment.

FIG. 3 illustrates the physiological sensor 104 in accordance with one embodiment. Like the environmental sensor 102, the physiological sensor 104 may be a multivariable gas sensor, or may optionally represent another version of the sensors or sensing systems described herein. In one or more embodiments, the physiological sensor 104 includes a physiological sensing element 302 having a substrate 304, such as a dielectric material, with a sensing film or physiological sensing material 308 coupled to the substrate 304. The physiological sensing material 308 is exposed to, in contact with, in indirect contact with, or the like, at least one analyte gas. One or several heating elements (not shown) may be optionally coupled with a different side of the substrate 304 that can receive electric current from a heater controller (not shown). The physiological sensing material 308 can include one or more materials deposited onto the substrate 304 to perform a function of predictably and reproducibly affecting the impedance sensor response upon interaction with the physiology of a subject of the physiological sensor 104.

Sensing electrodes 310, 312 are coupled with or disposed in the physiological sensing material 308 and are connected with the substrate 304 in the illustrated embodiment. The sensing electrodes 310, 312 are conductive bodies that are conductively coupled with the excitation assembly 120 of the control unit 106. The excitation assembly 120 applies a first electrical stimuli to the sensing electrodes 210, 212 of the environmental sensor 102 at one or more frequencies. Additionally, the excitation assembly 120 applies a second electrical stimuli to the sensing electrodes 310, 312 of the physiological sensor 104 at one or more frequencies. Non-limiting examples of the electrical stimuli include steady-state excitation, periodic excitation, pulsed excitation, custom-modulated excitation, thermal excitation, acoustic excitation, photonic excitation, or the like. The one or more processors of the excitation assembly 120 direct the sensing electrodes 210, 212 to apply the first electrical stimuli to the environmental sensing material 208 of the environmental sensor 102, and direct the sensing electrodes 310, 312 to apply the second electrical stimuli to the physiological sensing material 308 of the physiological sensor 104.

The first electrical stimuli may be applied to the environmental sensor 102 independent of (e.g., different frequency, different range of frequencies, different excitation methods, at different moments in time, or the like) the second electrical stimuli applied to the physiological sensor 104. For example, the first electrical stimuli may have a first frequency and may be applied as steady-state excitation stimuli, and the second electrical stimuli may have a different, second frequency, or may be a range of frequencies that may or may not include the first frequency, and may be applied as periodic excitation stimuli. Optionally, the excitation assembly 120 may apply common first and second electrical stimuli to the environmental sensor 102 and physiological sensor 104, respectively.

In the illustrated embodiment, excitation of the environmental and physiological sensors 102, 104 is performed by the single excitation assembly 120. In alternative embodiments, the sensor system 100 may include two or more excitation assemblies that may separately control the excitation of the sensing electrodes 210, 212 of the environmental sensor 102 and the sensing electrodes 310, 312 of the physiological sensor 104.

The one or more processors of the data acquisition circuitry 116 may receive an environmental electrical signal from the sensing electrodes 210, 212 and a physiological electrical signal from the sensing electrodes 310, 312. The environmental signals can represent the impedance or impedance response and/or a resistance or resistance response of the environmental sensing material 208 during exposure of the environmental sensing material 208 to the fluid sample. For example, the environmental signals may represent or be indicative of one or more environmental conditions that a subject may be exposed to or in operational contact with. The physiological signals can represent the impedance or impedance response and/or resistance or resistance response of the physiological sensing material 308 during exposure of the physiological sensing material 308 to one or more physiological and/or physical characteristics of the subject. For example, the physiological signals may represent or be indicative of one or more physiological parameters of the subject. The data acquisition circuitry 116 may process the environmental and physiological electrical signals via univariate and/or multivariate signal-processing, baseline correction, thresholding, integration, clustering, classification, quantitation, or the like.

The environmental sensor 102 can be a stationary sensor or device, can be transitory device such that the environmental sensor 102 can be moved from a first position to a different, second position, or the like. In one embodiment, the environmental sensor 102 can be disposed proximate to or set in a flow path of the fluid, such as coupled to in-line connectors in fluid communication with a fluid reservoir that defines a flow path. The environmental sensor 102 may be disposed proximate a fluid reservoir in a form of a vessel with controlled volume or in a form of an open area such as an indoor facility (e.g., a room, a hall, a house, a school, a hospital, or the like), or in the form of an outdoor facility (e.g., a stadium, a gas-production site, a construction site, a seashore, a forest, or the like). In one or more embodiments, the environmental sensor 102 may be disposed within a housing (not shown) that may be transferrable between different positions of the indoor and/or outdoor facility. For example, the environmental sensor 102 may be coupled with or placed proximate to (e.g., within a distance threshold) of a gas tank of a gas-production site. In another embodiment, the environmental sensor 102 may be a wearable device that may be worn by a human target. For example, the environmental sensor 102 may be coupled with an article worn by the subject (e.g., coupled with or integrated with shirt, pants, vest, eyeglasses, hats, hearing devices, or the like). In one embodiment, the environmental sensor 102 may be integrated with a wearable pulse oximeter system that may be in the form of an ear-piece or part of a frame of military, industrial, or consumer eyeglasses.

The physiological sensor 104 can be a stationary sensor or device, can be transitory device, such that the physiological sensor 104 can be moved from a first position to a different, second position, or the like. In one embodiment, the physiological sensor 104 can be coupled with a subject. For example, the physiological sensor 104 may be a wearable sensor or device that may be removably coupled or integrated with an article worn by the subject, such as a shirt, pants, safety vest, eyeglasses, hat, hearing devices, or the like. Optionally, the physiological sensor 104 may be coupled with the subject via an adhesive layer, such as medical tape. In another embodiment, the physiological sensor 104 may be coupled with or disposed proximate to (e.g., within a distance threshold) the subject, such as by a clip or any fastener.

In the illustrated embodiment of FIG. 1, the environmental sensor 102 and the physiological sensor 104 are separated from each other. Optionally, in one or more embodiments, the environmental sensor 102 and the physiological sensor 104 may be housed or held within a common housing. For example, the environmental sensor 102 and the physiological sensor 104 may be held in a package in the form of an ear-piece or part of a frame of military, industrial, or consumer glasses (e.g., eye glasses, protective eye glasses, or the like). In another embodiment, the environmental sensor 102 and the physiological sensor 104 may be The environmental signals received by the control unit 106 via the environmental sensor 102 are indicative of the one or more environmental conditions. For example, the environmental sensor 102 can detect at least one analyte of interest, particle matter contaminants, ultraviolet radiation exposure, ambient temperature, ambient atmospheric pressure, ambient relative humidity, sensor acceleration, or the like. The analyte of interest may be a gaseous analyte of interest, a liquid analyte of interest, or a gas-liquid mixture of an analyte of interest.

The physiological signals received by the control unit 106 via the physiological sensor 104 are indicative of the one or more physiological parameters. For example, the physiological parameters can include, but are not limited to, skin temperature, core body temperature, skin conductivity (e.g., sweat), blood pressure, systolic blood pressure variability, blood glucose, respiration rate, respiration rate variability, oxygen saturation, oxygen saturation variability, heart rate, heart rate variability, heart sounds, body movement (e.g., abduction, adduction, extension, flexion, rotation, and circumduction), muscle analysis, gait and gait analysis, brain activity, or the like, of a user, a patient, a subject, an operator, plural users, or the like, of the sensor system 100. The measured physiological parameters may be related to neural, respiratory, circulatory, cardiac, hemodynamic, and/or metabolic and other physiological functions of the subject.

Returning to FIG. 1, the sensor system 100 can also include a weather center 130. The weather center 130 may be configured to acquire one or more ambient parameters (e.g., wind direction and/or speed, temperature, humidity, or the like) based on the environment proximate to the sensor system 100. The weather center 130 may include an anemometer, thermometer, barometer, hygrometer, pyranometer, rain gauge, or the like. For example, the weather center 130 can acquire a wind speed, a wind direction, temperature, and/or the like, or a geographical area proximate the environmental sensor 102 and/or the physiological sensor 104. The weather center 130 may be communicatively coupled with the control unit 106 via one or more bi-directional communication links 126. The weather center 130 communicates one or more ambient parameters to the control unit 106. In one or more embodiments, data corresponding to the one or more ambient parameters from the weather center 130 may be synchronized with the environmental signals and/or the physiological signals to provide a more accurate sensor reading of the environmental parameters.

Figure 4:
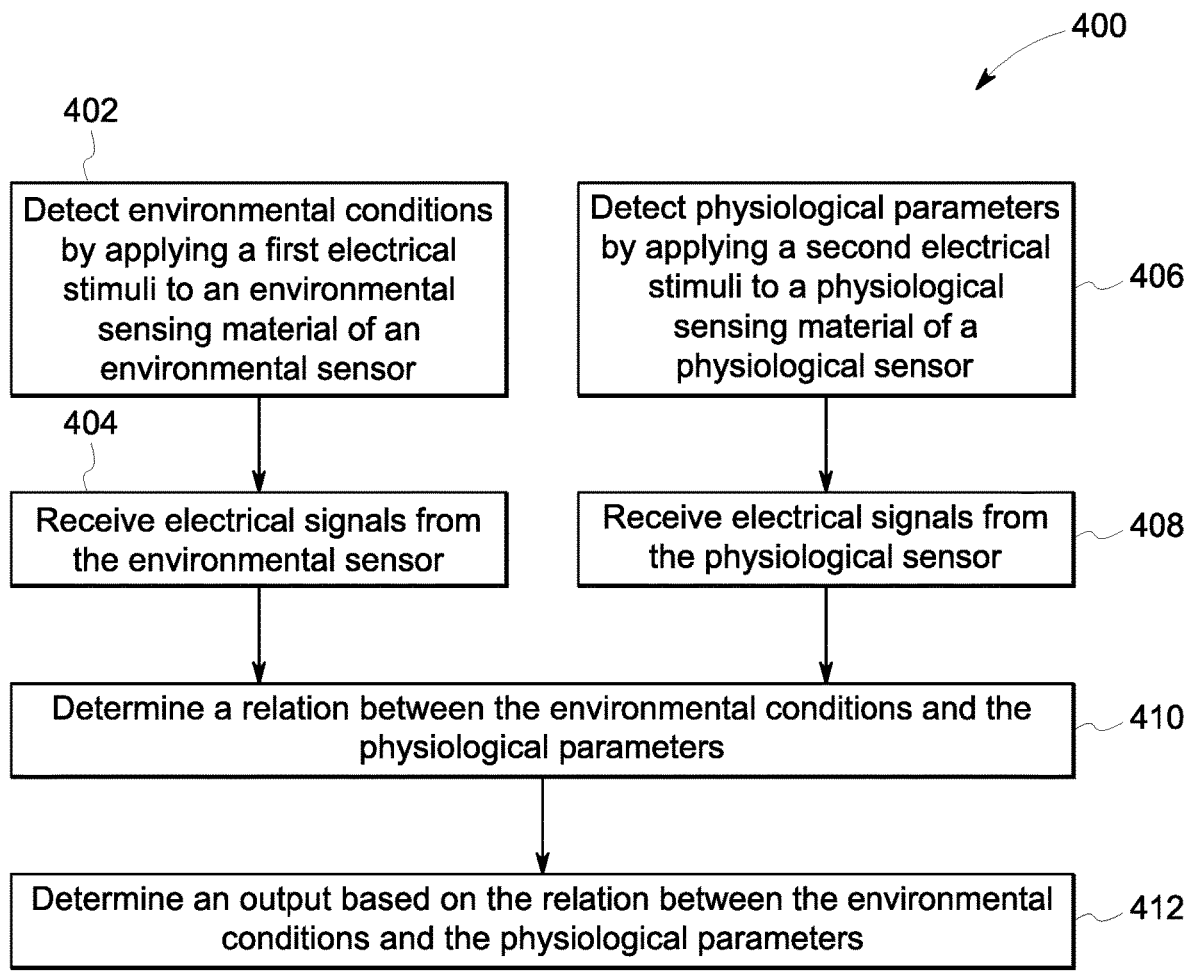
FIG. 4 illustrates a flowchart of one embodiment of a method for sensing environmental conditions and physiological parameters in accordance with one embodiment.

FIG. 4 illustrates a flowchart of a method 400 for sensing environmental conditions and physiological parameters in accordance with one embodiment. The method 400 can represent some of the operations performed by the sensor system 100 including the environmental sensor 102, the physiological sensor 104, and one or more processors of the control unit 106 described herein, or optionally can represent the operations performed by another sensing system and/or other sensors. For example, the method 400 can represent operations performed by the sensor system 100 under direction of one or more software applications, or optionally can represent an algorithm useful for writing such software applications.

At 402, the excitation assembly 120 applies first stimuli to the environmental sensing element 202 via the sensing electrodes 210, 212 of the environmental sensor 102. Responsive to applying the first stimuli, the environmental sensor 102 detects one or more environmental conditions of the environment in operational contact with the subject. The control unit 106 can control the excitation assembly 120 to control the first stimuli applied to the environmental sensing element 202. In one or more embodiments, the environmental sensor 102 can detect the environmental conditions of the environment in operational contact with the subject with plural different detection resolutions. At 404, the control unit 106 receives environmental electrical signals from the environmental sensor 102 indicative of the one or more environmental conditions detected by the environmental sensor 102.

At 406, the excitation assembly 120 applies second stimuli to the physiological sensing element 302 via the sensing electrodes 310, 312 of the physiological sensor 104. Responsive to applying the second stimuli, the physiological sensor 104 detects one or more physiological parameters. The control unit 106 can control the excitation assembly 120 to control the second stimuli applied to the physiological sensing element 302 of the physiological sensor 104. In one or more embodiments, the physiological sensor 104 can detect the physiological parameters of the subject in operational contact with the asset with different detection resolutions. At 408, the control unit 106 receives physiological electrical signals from the physiological sensor 104 indicative of the one or more physiological parameters detected by the physiological sensor 104.

In one embodiment, at least portions of the environmental sensor 102 and/or the physiological sensor 104 may operate in a low-power mode or in a stand-by mode while other portions of the environmental sensor 102 and/or the physiological sensor 104 operate in a normal operation mode. Sensors 102 and/or 104 that operate in a normal operation mode may detect an environmental and/or physiological condition, respectively, that may require to bring the rest of the sensor 102 and/or 104 from the low-power or stand-by mode to the normal operation mode. Based on the responses of the sensors 102, 104, additional sensors can be on-demand turned on to the normal operation mode from an off-mode, the low-power mode, and/or the stand-by mode. Such on-demand addition of sensors can be based on prioritization, adaptative, and/or situational analysis. Optionally, the environmental sensor 102 and/or the physiological sensor 104 may change between operating in a relatively-high-sensitivity mode and operating in a relatively-low-sensitivity mode. For example, the environmental sensor 102 may detect or sense different environmental conditions when the environmental sensor 102 is operating in the relatively-high-sensitivity mode relative to when the environmental sensor 102 operates in the relatively-low-sensitivity mode.

In one or more embodiments, the steps 402, 404 and 406, 408 may be performed substantially simultaneously or may be performed at different times. Optionally, the data corresponding to the environmental signals and the physiological signals may be time stamped such that the control unit 106 can identify and coordinate the environmental conditions and the physiological parameters corresponding to a common moment in time.

The control unit 106 receives the one or more environmental signals from the environmental sensor 102 and receives the one or more physiological signals from the physiological sensor 104 and at 410, the control unit 106 determines a relation between the environmental conditions (indicated by the environmental signals) and the physiological parameters (indicated by the physiological signals). The relation between the environmental conditions and the physiological parameters is based on the environmental signal and the physiological signal.

The combinations of individual measured parameters of sensors 102 and/or sensors 104 can be further analyzed using known statistical methods such as multivariate methods and chemometric methods. Nonlimiting examples of such methods include principal components analysis, partial least squares, support vector machine, or the like. Such analysis may be performed by the control unit 106. The control unit 106 can be on-board with either sensor 102 or sensor 104, or can be in a central remote location (e.g., in a cloud center).

In one or more embodiments, the combination of individual measured parameters of sensor 102 and/or sensor 104 can also be analyzed using additional inputs from contextual factors. The contextual factors may be personal, with nonlimiting examples of age and gender of the subject. Alternatively, the contextual factors may be environmental, with nonlimiting examples of physical environmental parameters, social parameters, and/or local parameters. The nonlimiting examples of local parameters can include schedules of local businesses, municipal waste pickup, information about past or previous events of chemical or other spills or leaks in the area proximate the subject and or the system 100, elevated levels of pollutants and/or types of pollutants and other details that can positively or negatively affect the subject, or the like. Results of such analysis can be used to furnish a multidimensional assessment score or pallet of the subject. This can be a simple numerical indicator or a color-coded value within a range of colors. Such a multidimensional score can facilitate controls of the one or more assets in operational contact with the subject and/or to control a schedule of the subject and/or a schedule of the asset. Additionally or alternatively, the score can be communicated across a network of subjects/assets to serve as an alert or indicator.

In one or more embodiments, the control unit 106 can also receive one or more ambient parameters from the weather center 130. The control unit 106 may determine a relation between the environmental conditions, the physiological parameters, and the ambient parameters.

At 412, the control unit 106 determines an output based on the relation between the environmental conditions and the physiological parameters. The output may include internal and/or external actions or activities to be performed by the subject. Internal actions may include taking medication, to move, to sleep, to eat and/or drink, notification to see a doctor, or the like. External actions may include apply physical activity to operate a device, apply physical activity to move the body or parts of the body of the subject, or the like. The output may be communicated to the subject via the input/output device 114, such as a message, an alarm, a flashing or blinking light, the change of a color of a light, or the like. Optionally, the control unit 106 may determine that no action or activity is required based on the relation between the environmental conditions and the physiological parameters. The input/output device 114 may display an output message that no action is needed, may not display any additional message or alarm, or the like. The method 400 returns to steps 402 and 406 and can repeat until a threshold is met. For example, the method 400 may continue to repeat while the subject is within a predetermined distance of a gas-production site or a predetermined distance of a military zone.

In one embodiment, the wearable sensor data may be enhanced when augmented with its geographical and/or vertical location. In one nonlimiting example, a wearable seismic sensor can send data with knowledge of where the closed fault line in that can help to provide directionality of an event. The seismic data from the sensor can further be augmented to provide a location of first aid equipment and/or services, direction to a safe exit, or the like. In one nonlimiting example, a wearable electric fault sensor can send data with knowledge of location of a service or access panel. In another nonlimiting example, a radiation reading can be performed using a wearable sensor with context to nearby a source of a reactor or other radiation sensors nearby or within a proximate distance. In another nonlimiting example, a detected fluid leak can be mapped to a fluid reservoir or to a blueprint of an asset that contains the fluid. In another nonlimiting example, a wearable flood sensor reading can provide direction to higher or elevated ground. In another nonlimiting example, wearable gas sensors can map location of storage facilities, occupied buildings, potential sources of gas ignition, or the like. The augmented map along with any wearable sensor data can guide best action to take and/or avoid making a wrong move that could make problems worse, delay rescue, or other activities.

Similar to human subjects, robot or robotic subjects can be affected by the environment. The surrounding environment could degrade, report misleading information, or render inoperative key systems meant to protect or assist human and robot subjects. It becomes apparent that robots require sensor that ensure the robot subjects are reliable and intended behavior. In case of robot subjects, physiological parameters may mean, represent, or imply physical and/or chemical status parameters of the operation condition of the robot subjects. An aerial drone robot sensing gas may be affected by wind pattern influencing air concentrations, rain, heat, or a basic ability to maintain flight. Bright lights may saturate camera systems and prohibit use of visual navigation. In case of underwater drone robot subjects, nonlimiting examples of the awareness of conditions that may produce harm may include tsunami warnings, currents, ice or frozen masses, hot springs, or the like. The sensors may inform the risk of a change of status parameters of the operation condition of the robot subject. Presence of radiation, rain, low/high temperatures, air pollution, or other harsh environmental conditions may also negatively affect the accuracy and lifetime of sensors that report the status parameters of the operation condition of the robot subject.

Figure 5:
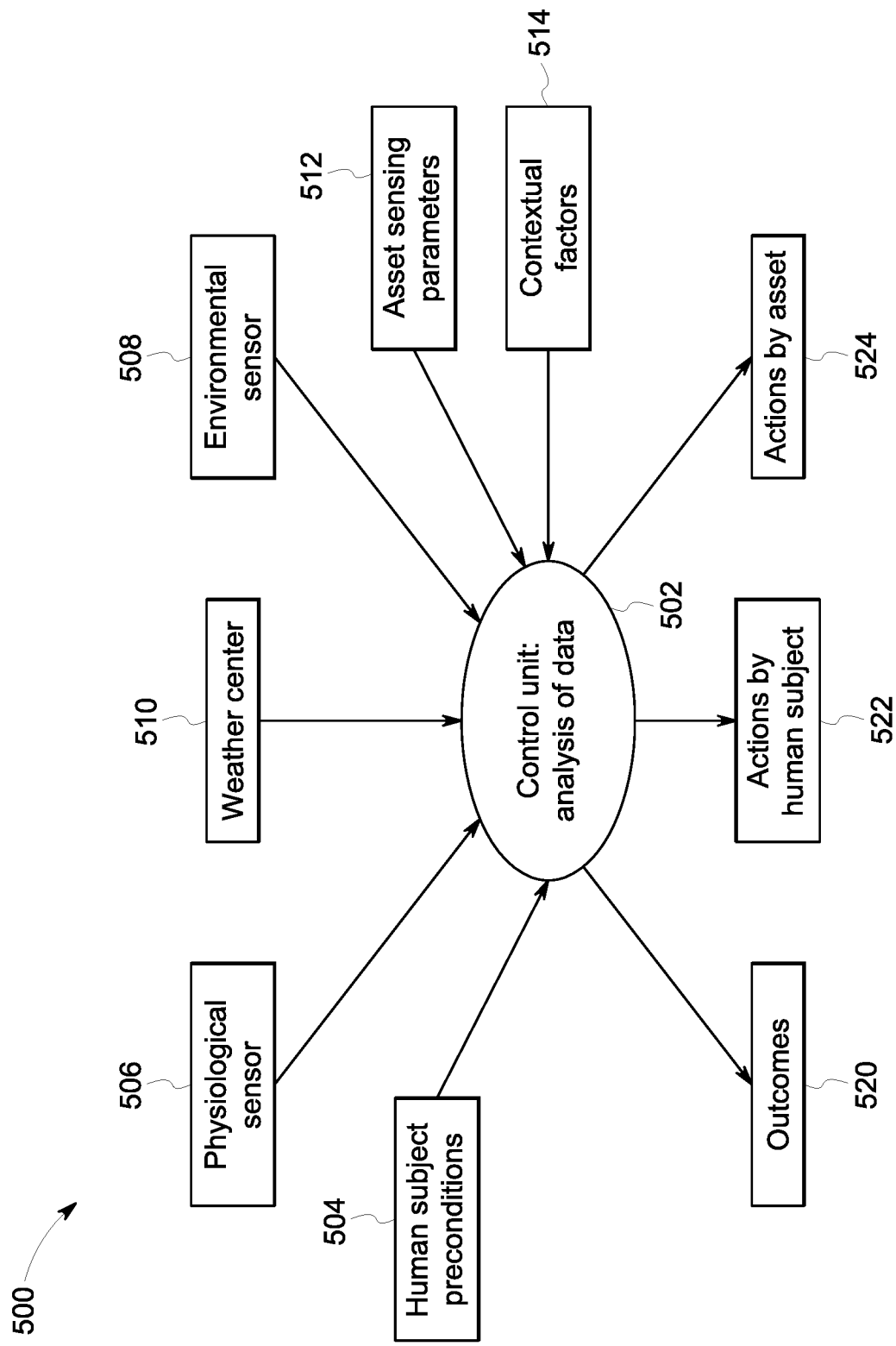
FIG. 5 illustrates an input and output chart for operating a sensor system in accordance with one embodiment.

FIG. 5 illustrates an input and output chart 500 for operating the sensor system 100 in accordance with one embodiment. The control unit 106 receives one or more inputs sources. The one or more processors of the control unit 106 may analyze the data received from the plural inputs and outputs one or more output responses. The control unit 106 receives heterogeneous data from one or more of the inputs (e.g., sensors, actions by a subject wearing or proximate to the sensors, actions by the environment or an asset that is associated with the subject) and analyzes the heterogeneous data from the inputs. As a result of determining a correlation or relation between the environmental and physiological sensors, the control unit 106 can determine one or more outputs, such as directing the subject to perform some actions or activities or actions to be taken by the environment or by the asset in relation to the subject.

The control unit 502 can receive data from one or more input sources, such as a first input source 504 (e.g., subject preconditions), a second input source 506 (e.g., physiological signals from the physiological sensor indicative of physiological parameters of the subject), a third input source 508 (e.g., environmental signals from the environmental sensor indicative of environmental conditions), a fourth input source 510 (e.g., ambient parameters from the weather center), a fifth input source 512 (e.g., known asset sensing parameters), and a sixth input source 514 (contextual factors). The illustrated embodiment includes five different input sources. Optionally, the control unit 106 may receive data from less than five or more than five different sources.

The first input source 504 may represent preconditions of the subject. The preconditions can include chemical information, physical information, medical information, or the like. In one or more embodiments, the first input source 504 can also communicate asset and/or environmental information to the control unit 502, such as a geographical location, an asset associated with the subject such as a medical device, or the like. In one or more embodiments, the subject may take in or receive energy and/or resources, and the energy and/or resource information may be communicated to the control unit 106. In another embodiment, the subject may expel one or more different exhausts, and the exhaust information may be communicated to the control unit 106.

The second input source 506 may represent the physiological sensor (illustrated in FIGS. 1 and 3). The physiological sensor 104 may transmit one or more physiological parameters that may be indicative of known physiological parameters, excitation conditions, stimulation of the subject, dynamic signatures, detection between electrical stimulations, or the like. The physiological sensor 104 may be a wearable sensor device to detect the one or more physiological parameters of the subject or plural subjects, may be a transferrable sensor device that can be moved between different positions (e.g., a device that can be removably coupled with the subject, a device that the subject can sit or lay on, or the like), may be a stationary or substantially stationary sensor device, or the like.

The third input source 508 may represent the environmental sensor (illustrated in FIGS. 1 and 2). The environmental sensor 102 may transmit one or more environmental conditions that may be indicative of one or more analytes of interest, particle matter contaminants, ultraviolet radiation exposure, ambient temperature, ambient atmospheric pressure, ambient relative humidity, sensor acceleration, or the like. The environmental sensor 102 may be a wearable sensor device, may be a transferrable sensor device that can be moved between different positions, may be a stationary or substantially stationary sensor device, or the like. In one or more embodiments, the physiological sensor 104 and the environmental sensor 102 may be held within a common housing, such as an ear piece or eye-glasses. Optionally, the physiological sensor 104 and the environmental sensor 102 may be held within separate and distinct housings from each other.

The fourth input source 510 may represent the weather center 130 (illustrated in FIG. 1). The weather center 130 may transmit one or more ambient parameters to the control unit 106 that may be indicative of an ambient temperature, ambient pressure, ambient humidity, or the like.

The fifth input source 512 may represent asset sensing parameters that may be transmitted via an asset associated with the subject. The asset may be a hospital bed, a motorized and/or a non-motorized vehicle, a system of an industrial site (e.g., a turbine engine, a gas vessel, or the like), or the like.

The sixth input source 514 may represent contextual factors that may be personal, with nonlimiting examples of age and gender. The contextual factors may also be environmental, with nonlimiting examples of physical environmental parameters, social parameters, and local parameters. The nonlimiting examples of local parameters can be schedules of local businesses and municipal waste pickup information, information about past events of chemical and other spills and/or leaks in the proximate geographical area, elevated levels of pollutants and types of pollutants and other details that can positively and/or negatively affect the subject, or the like. Results of such analysis can be used to furnish a multidimensional assessment score or pallet of the subject. This can be a simple numerical indicator or a color-coded value within a range of colors. Such a multidimensional score can facilitate controls of the one or more assets in operational contact with the subject and/or to control a schedule of the subject and/or a schedule of the asset. Additionally or alternatively, the score can be communicated across a network or subjects and/or assets to server as an alert or indicator.

The one or more processors of the control unit 106 analyze all of the data received via electrical signals from each of the input sources, and determines a relation between the data. In one or more embodiments, one of the input sources may transmit plural electrical signals, the control unit 106 may receive electrical signals from one or more of the input sources, may receive electrical signals from each of the input sources, or any combination therein.

Figure 6:
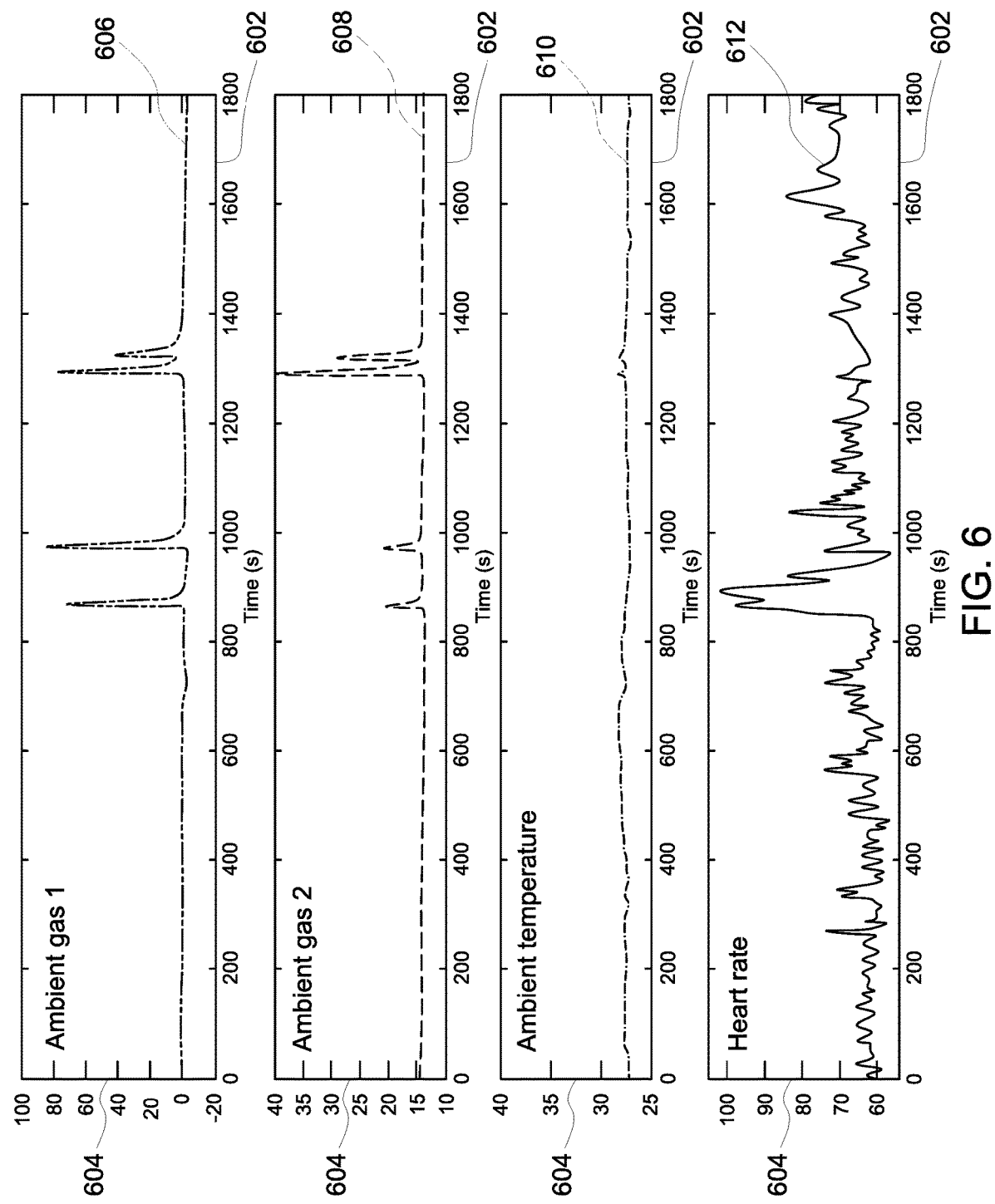
FIG. 6 illustrates a graphical illustration of a relation between data received from input sources in accordance with one embodiment.

FIG. 6 illustrates a graphical illustration of a relation between data received from input sources in accordance with one embodiment. The data is received by the control unit 106 as electrical signals. The electrical signals are shown alongside a horizontal axis 602 representative of time and a vertical axis 604 representative of the magnitudes of the electrical signals. A first electrical signal 606 can represent a first environmental signal received from an environmental sensor and a second electrical signal 608 can represent a second environmental signal received from the same or a different environmental sensor as the first electrical signal 606. The first electrical signal 606 is indicative of a first environmental condition (e.g., a first ambient gas), and the second electrical signal 608 is indicative of a second environmental condition (e.g., a second ambient gas that is different than the first ambient gas).

A third electrical signal 610 can represent an ambient parameter, such as ambient temperature. The control unit 106 may receive the third electrical signal 610 via the weather center 130, or an alternative source. A fourth electrical signal 612 can represent a physiological signal received from a physiological sensor. The fourth electrical signal 612 is indicative of a physiological parameter (e.g., heart rate) of the subject.

Figure 7:
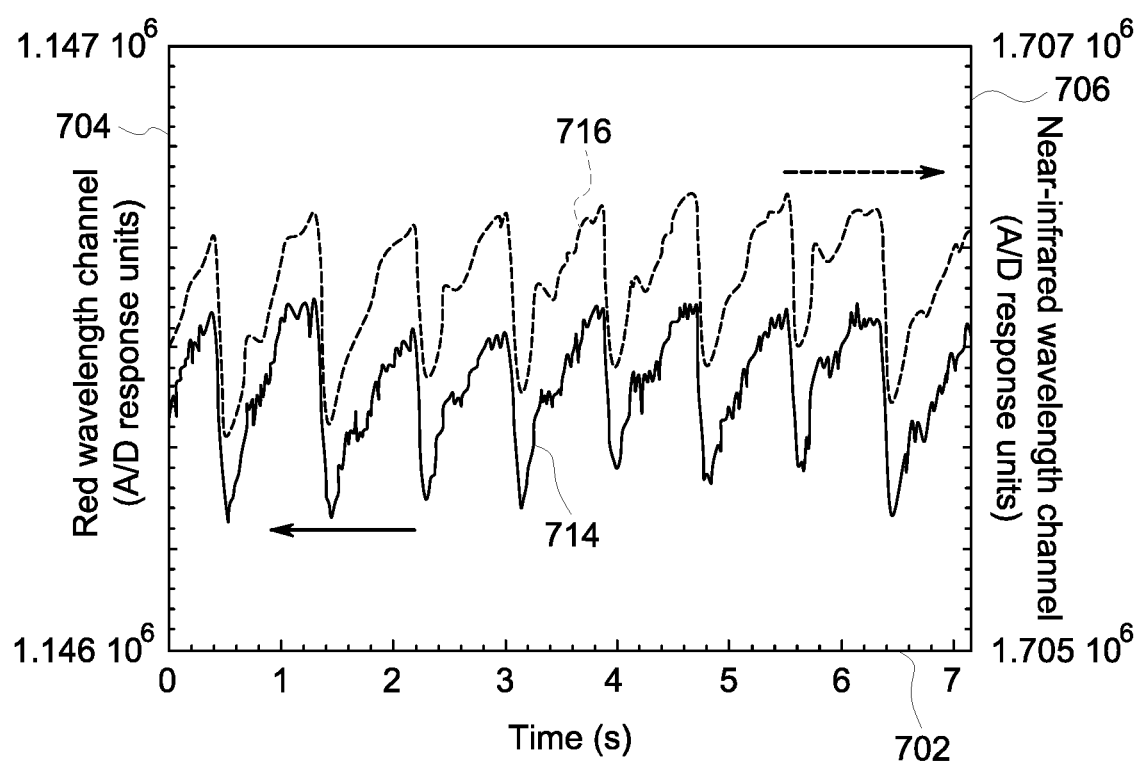
FIG. 7 illustrates another graphical illustration of a relation between data received from input sources from a wearable sensor in accordance with one embodiment.

FIG. 7 illustrates another graphical illustration of a relation between data received from input sources from a wearable sensor in accordance with one embodiment. The data is received by the control unit 106 as electrical signals. The electrical signals are shown alongside a horizontal axis 702 representative of time and vertical axis 704 and 706 representative of the magnitudes of the electrical signals. In one embodiment, a first electrical signal 714 can represent a first signal received from a physiological sensor, and may represent a pulse oximeter response from a subject measured with a red wavelength channel and displayed as response units from an analog-to-digital (A/D) converter. A second electrical signal 716 can represent a second signal received from the same physiological sensor, and may represent a pulse oximeter response from a subject measured with a near-infrared wavelength channel and displayed as response units from an A/D converter. Different baseline levels and amplitudes of the two signals 714, 716 at two wavelengths may be related to the blood oxygenation of the subject. Optionally, the two wavelengths may be related to an alternative physiological parameter of the subject. The consecutive valleys of the waveforms may be related to the heart rate of the subject. The physiological sensor may operate with a data acquisition speed of about 100 measurements per second to capture the waveform of the pulse of the subject that has a relatively short time constants. Optionally, the physiological sensor may operate at a speed that is slower or faster than 100 measurements per second. For example, the features of the waveform may be further determined using known methods that may be reported and/or displayed using a slower data reporting or display speed of about once per second. The reporting and/or display speed may be approximately similar to the data acquisition speed of other sensors in the sensor system.

Returning to FIG. 6, the control unit 106 determines a relation between the first and second, electrical signals 606, 608. In the illustrated embodiment, the electrical signals are aligned with each other along the horizontal axis 602 representative of time. For example, each of the electrical signals are graphed at the same or common time as each other electrical signal to determine the relation between each of the electrical signals. In alternative embodiments, the relation between each of the electrical signals may be determined by an alternative method.

Figure 8:
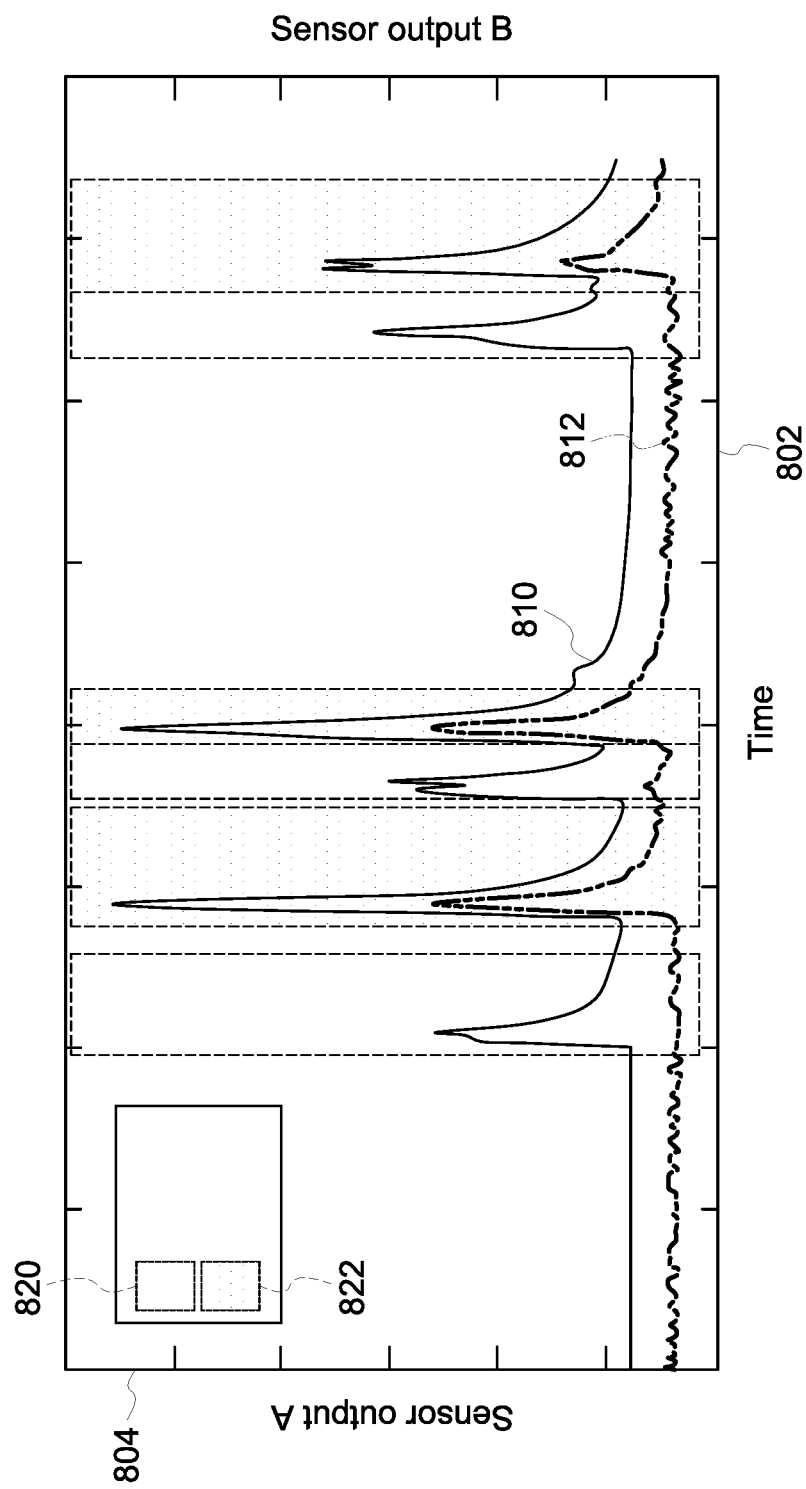
FIG. 8 illustrates a graphical illustration of another example of a relation between data received from input sources in accordance with one embodiment.

FIG. 8 illustrates a graphical illustration of another example of a relation between data received from input sources in accordance with one embodiment. The data is received by the control unit 106 as electrical signals where two different gases produce different dynamic responses of a single environmental sensor. The single environmental sensor 102 has two distinctly different electrical signal outputs. The electrical signals are shown alongside a horizontal axis 802 representative of time and a vertical axis 804 representative of a magnitude of the electrical signals. A first environmental signal 810 can represent a first environmental condition received from an environmental sensor, and a second environmental signal 812 can represent a second environmental condition from the same environmental sensor as the first environmental signal 810. As illustrated in FIG. 8, the first environmental signal 810 responded to a first gas 820 and a second gas 822. Alternatively, the second environmental signal 812 responded to the first gas 820 but did not respond to the second gas 822.

Returning to FIG. 5, the control unit 106 determines one or more outputs based on the relation determined between each of the electrical signals received via one or more of the input sources. The outputs may be a first output 520, such as outcomes, a second output 522, such as actions or activities to be taken by the subject, a third output 524, such as actions or activities to be taken by the asset, or the like. Optionally, the control unit 106 may determine an alternative output (e.g., action, activity, or the like) to be taken by a second subject, an alternative sensor system, any alternative system, or the like.

The first output 520 that is determined by and/or output by the control unit 106 may include diagnostic and/or prognostic information of the subject and/or the asset. Optionally, the outcome 520 may include direction to observe the subject, observe the asset, or observe the control unit 106 for additional analysis. Optionally, the outcome 520 may include directions to control a system, feature, or the like, of the subject and/or the asset. The outcomes 520 may be communicated to a user of the sensor system 100 via the input/output device 114, such as a message, an alarm, a light, or the like.

The second output 522 determined by and/or output by the control unit 106 may include actions or activities to be taken by the subject, such as internal and/or external actions or activities. The internal actions can include to induce a different state or to induce a different activity, such as to take a medication, to move, to sleep, to eat and/or drink, directions to see a doctor, or the like. The external actions can include to apply physical activity to operate a device, to apply physical activity to move the body or parts of the body of the subject, or the like.

The third output 524 determined by and/or output by the control unit 106 may include actions or activities to be taken by the asset, such as asset control, such as changing the asset from manual control to autopilot or auto-control, to turn the asset off or on (e.g., stop an engine system, to park a vehicle, or the like), to change a setting of the asset (e.g., reduce an operating speed, increase an operating speed, to increase or decrease braking efforts, or the like.

Figure 9:
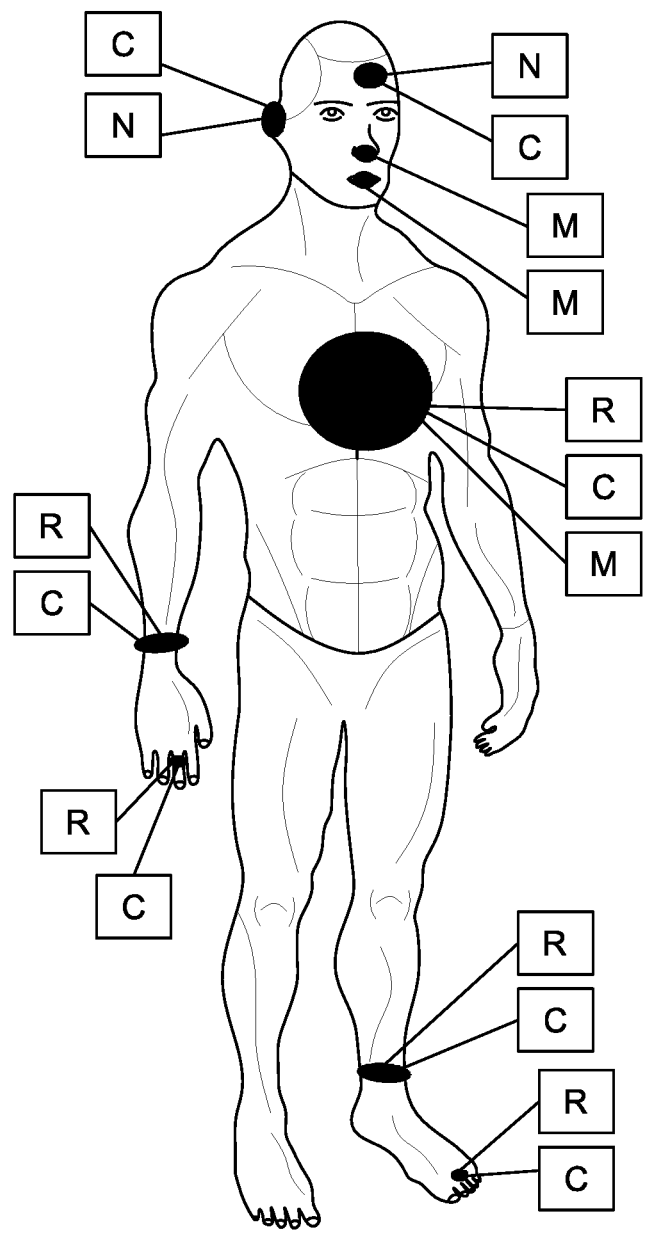
FIG. 9 illustrates exemplary positions of different wearable physiological sensors for monitoring physiological parameters of a subject in accordance with one embodiment.

FIG. 9 illustrates exemplary positions of different wearable physiological sensors 104 for monitoring physiological functions of the subject. The physiological parameters can include neural (N), respiratory (R), circulatory (C), and/or metabolic (M) physiological functions of the subject. Other physiological functions of the subject can also be determined, for example, cardiac and hemodynamic functions. Nonlimiting examples of positions of such sensors include an earlobe, forehead, chest, wrist, finger, or the like. Nonlimiting examples of measured physiological parameters as related to physiological functions include pulse oximetry parameters for neural function, respiratory rate parameters for respiratory functions, heart rate and heart variability parameters for circulatory function, body core temperature and/or hydration parameters for metabolic functions, or the like. In the illustrated embodiment of FIG. 9, the subject is a human subject, however the subject may be a mammal subject, a plant subject, or the like.

Figure 10A:
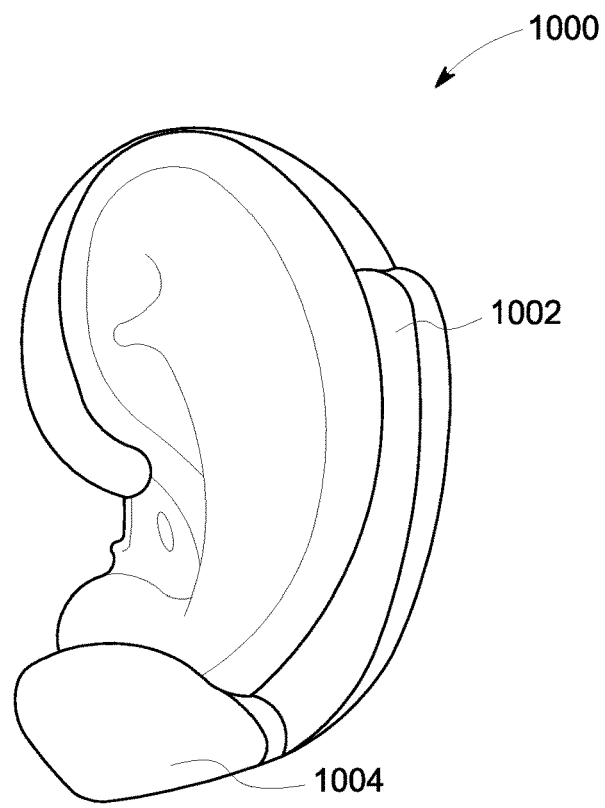
FIG. 10A illustrates a general view of an environmental and physiological sensor package in accordance with one embodiment.
Figure 10B:
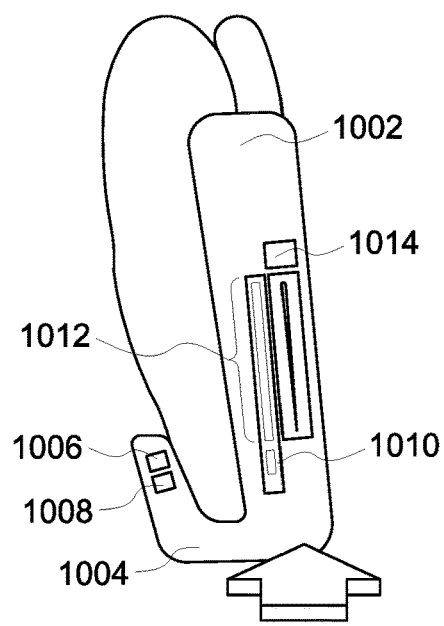
FIG. 10B illustrates design schematics of the sensor package illustrated in FIG. 10A.
Figure 10C:
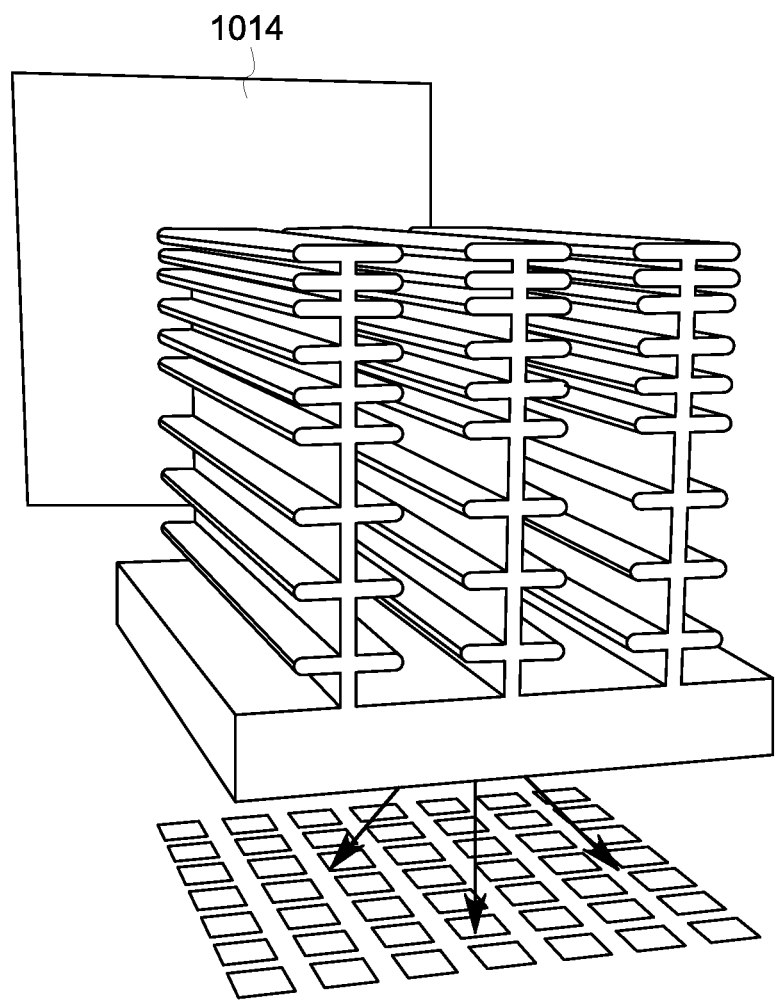
FIG. 10C illustrates an example of illumination of the sensor package illustrated in FIG. 10A.

FIGS. 10A-10C illustrate one example of a wearable detector package 1000 with an environmental sensor (e.g., photonic gas sensor) and a physiological sensor (e.g., pulse oximeter). FIG. 10A illustrates a general view of the wearable detector package 1000, FIG. 10B illustrates design schematics with shared electronic circuitry between the environmental sensor and the physiological sensor components, and FIG. 10C illustrates examples of illumination of the environmental sensor (e.g., the photonic gas sensor) and detection of dispersed light.

In the illustrated embodiment of FIGS. 10A-10C, an environmental gas sensor 1002 is integrated with a wearable physiological sensor 1004 (e.g., a pulse oximeter) to form a gas/physiological sensor package 1000. In the illustrated embodiment, the package 1000 is in the form of an ear-piece as depicted in FIG. 10A, or as part of a frame of military, industrial, or consumer eyeglasses, as depicted in FIG. 10B. The sensor package 1000 includes a transmission-based pulse oximeter operated using LED lights 1006, 1008 at about 600-700 nanometers (nm), and about 800-900 nm with monitoring intensities of light transmitted through the ear lobe by a photodiode 1010. Optionally, the sensor package 1000 may operate using LED lights 1006, 1008 at different monitoring intensities. The sensor package 1000 also includes a photonic gas sensor operated using a white LED 1014 with its reflective spectrum modulated by a gas and monitored by a photodiode array, including the photodiode 1010 for the pulse oximetry and a photodiode 1012 for chemical detection, as illustrated in FIG. 10B.

As illustrated in FIG. 10C, photonic gas sensor and pulse oximeter components can share the light-intensity stabilization and temperature compensation circuitry, photodetector electronics, and/or power for operation and wireless communication. The photonic gas sensor can be based on bio-inspired gas-sensing principles where a three-dimensional nanostructure can be fabricated as schematically shown in FIG. 10C. The nanostructure can respond to different gases in the ambient environment that is in operational contact with the subject. The nanostructure can be chemically functionalized with gas-sorbing layers, for example, silane, fluorinated polymer, and others, to change the optical pathlength of light that can be utilized to illuminate this nanostructure. The illumination light can reflect from the nanostructure and can produce a spectrum detected by the photodiode array. The relative intensities of light detected by individual elements of the photodiode array can be correlated to the concentrations of a single gas or multiple gases in the ambient environment in operational contact with the subject.

Wearable physiological sensors may have a degraded quality of signal as compared with hospital physiological measurement equipment. The origins of such quality of degradation include non-ideal electrode contact with the subject and movements of the subject during measurements of the physiological response. A hospital physiological measurement equipment serves as a standard measurement because in such a measurement, the electrodes are connected to the skin of the subject via a gel or other means to ensure a substantially perfect electrical contact. Further, the subject is asked not to move during measurements to avoid signal artifacts caused by movement.

Figure 11A:
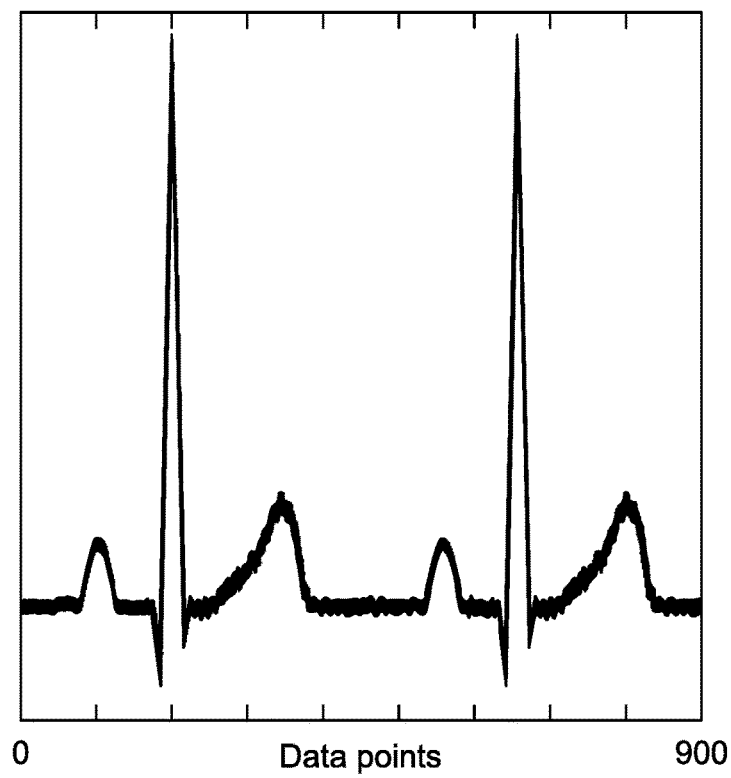
FIG. 11A illustrates a graphical illustration of a high-quality electrocardiogram (ECG) signal in accordance with one embodiment.
Figure 11B:
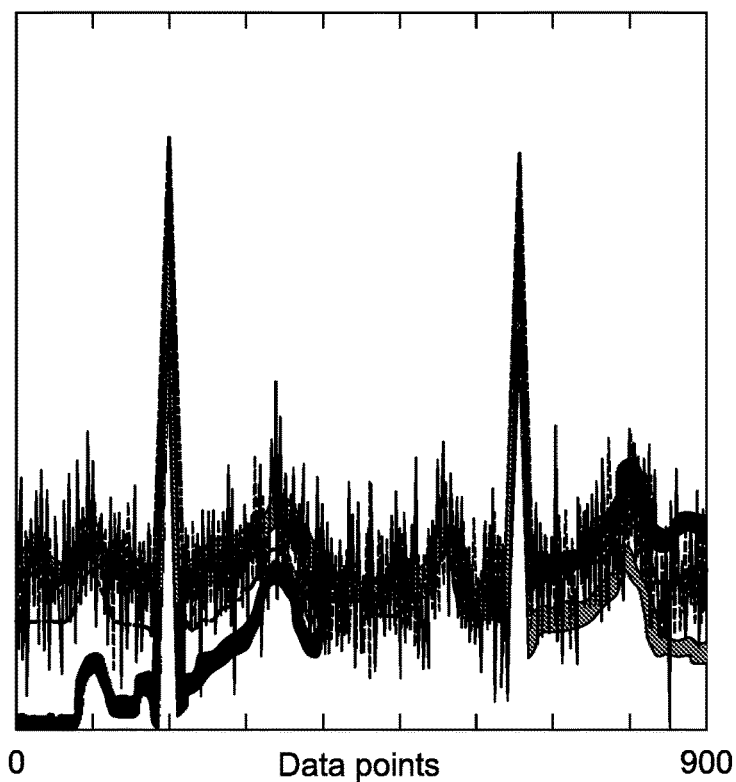
FIG. 11B illustrates a graphical illustration of ECG signals in the presence of poor electrode connection to a subject and electrode movement in accordance with one embodiment.
Figure 11C:
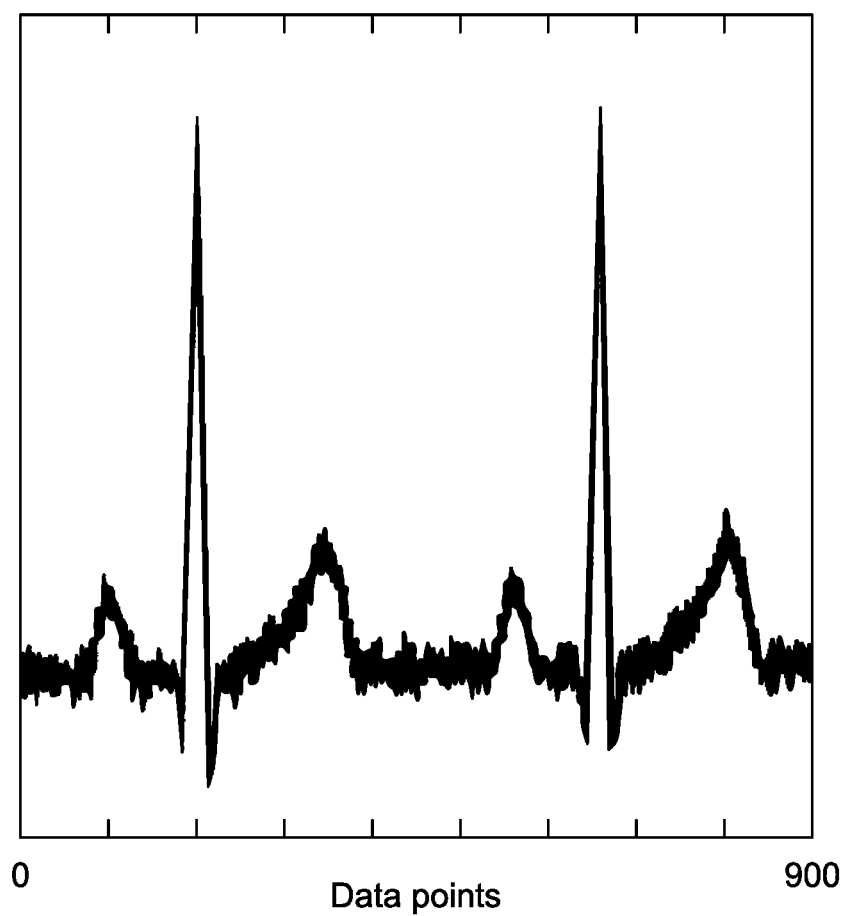
FIG. 11C illustrates a graphical illustration of data analysis to improve a quality of an ECG signal in the presence of poor electrode connection to a subject and electrode movement in accordance with one embodiment.

A graphical illustration of an example of a high-quality electrocardiogram (ECG) signal (e.g., from a hospital equipment) is illustrated in FIG. 11A, illustrating two cycles of ECG trace. However, as described, different artifacts degrade the quality of the ECG signal because of the poor electrode connection to the subject and/or electrode movements. The ECG signals in the presences of one or more of these conditions that induce practical artifacts are illustrated in FIG. 11B. By applying data analysis tools, such as machine learning tools, the practical artifacts are rejected, as illustrated in FIG. 11C. This example demonstrates that the quality of the data collected by or with a wearable physiological sensor 104 (e.g., as illustrated in FIG. 11C) can approach the data collected without artifacts (e.g., as illustrated in FIG. 11A), for example as collected using hospital equipment.

In one embodiment, a sensor performed measurements of different ions in a sample. Different types of ions may be determined in different samples, such as for example, blood, sweat, tears, saliva, urine, and other types of bodily fluids. Different concentrations of ions affect the conductivity of the sample. To detect the type of ions, typically ion-selective electrodes are utilized. By using a multivariable sensor, the different types of ions can be determined. A multivariable sensor may be in a form of a radio-frequency sensor such as a resonant impedance sensor.

The measured resonant impedance may be in a form of a spectrum with values of $Z'(f)$, which may be the real part of resonant impedance spectrum $Zre(f)$ and $Z''(f)$, which may be the imaginary part of resonant impedance spectrum $Zim(f)$ reflecting the response of the environmental sensor 102 to the fluid over a predetermined frequency range (f). Some parameters may be calculated from the measured $Zre(f)$ and $Zim(f)$ spectra such as the frequency position $F_p$ and magnitude $Z_p$ of $Zre(f)$ and the resonant $F_1$ and anti-resonant $F_2$ frequencies, and their magnitudes $Z_1$ and $Z_2$ of $Zim(f)$. While details of calculations of these parameters are previously disclosed, for example in U.S. Pat. No. 10,260,388 and details of using sensing films for detection of different ions in water are disclosed in U.S. Pat. No. 9,589,686, both of which are herein incorporated by reference, it is unexpectedly discovered that different ions can be discriminated without having a sensing film but using a resonant impedance sensor and analyzing the $F_p$, $Z_p$, $F_1$, $F_2$, $Z_1$, and $Z_2$ using known statistical tools. Different ions and their concentrations were prepared for measurements in the form of aqueous common buffers. Buffer solutions include buffer #1: sodium chloride (NaCl), five prepared replicate buffers; buffer #2: saline sodium citrate (SSC), three prepared replicate buffers; buffer #3: tris buffered saline (TB S), three prepared replicate buffers; buffer #4: phosphate buffered saline (PBS), one available buffer; and buffer #5: potassium chloride (KCl), three prepared replicate buffers. Measurements were performed at an ambient laboratory environment without temperature control during the measurements.

Figure 12A:
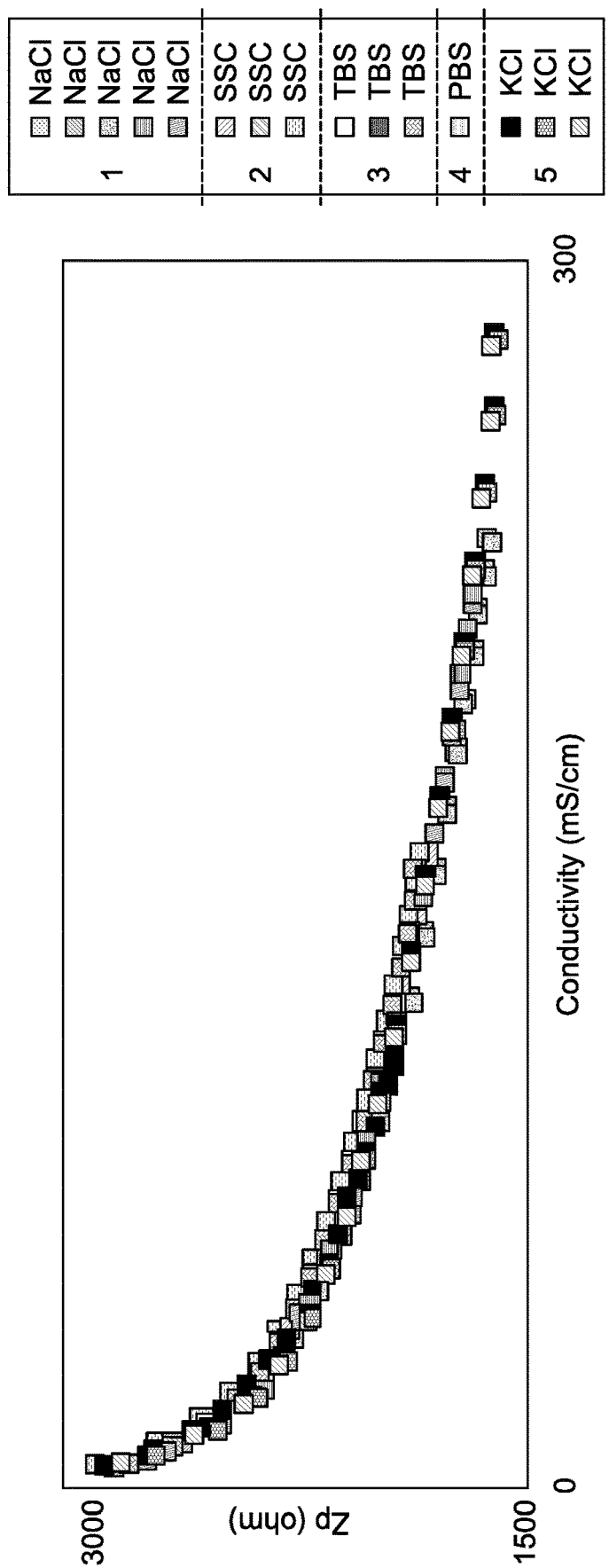
FIG. 12A illustrates an example of detection of five different types of ions in aqueous samples using conductivity measurement in accordance with one embodiment.

FIG. 12A illustrates an example of detection of five different types of ions (1-5) in aqueous samples using conductivity measurement such as Zp response of the resonant impedance sensor. FIG. 12A shows that conventional conductivity measurement cannot discriminate between the different types of ions (1-5).

Figure 12B:
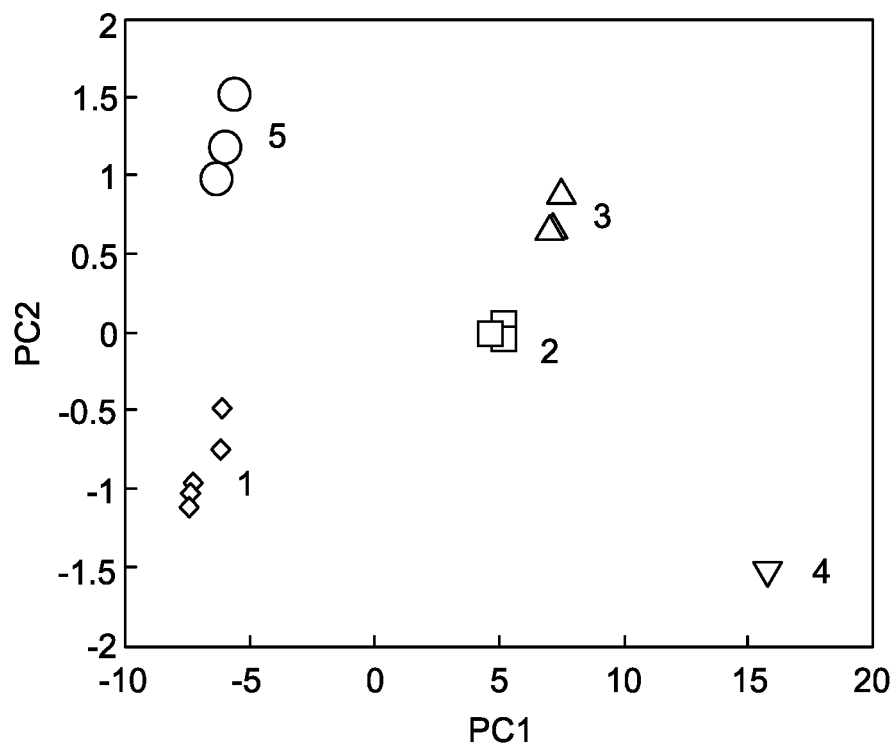
FIG. 12B illustrates an example of detection of five different types of ions in aqueous samples using plural outputs from a multivariable sensor with sensor data processed using principal components analysis and displayed as a two-dimensional scores plot.
Figure 12C:
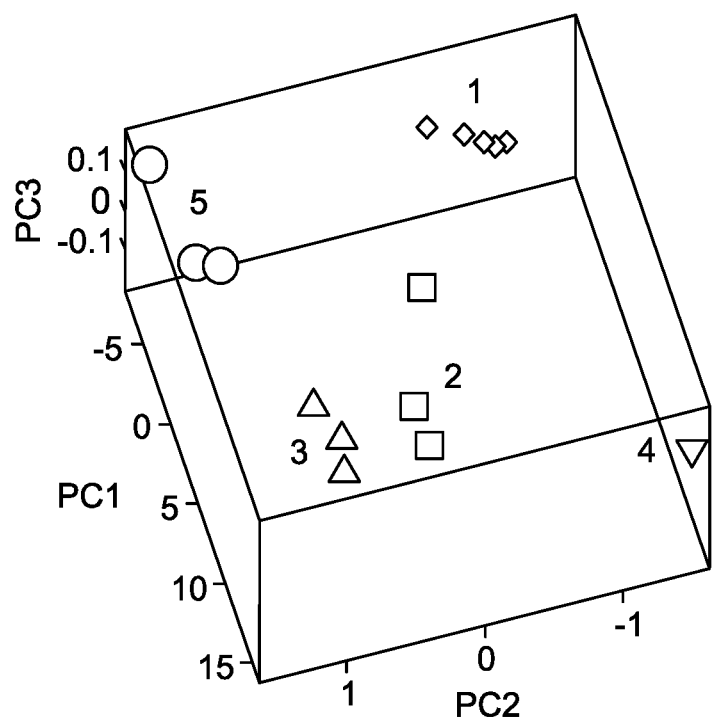
FIG. 12C illustrates an example of detection of five different types of ions in aqueous samples using plural outputs from a multivariable sensor with sensor data processed using principal components analysis and displayed as a three-dimensional scores plot.

FIG. 12B illustrates detection of the five different types of ions (1-5) in aqueous samples using plural outputs from a multivariable resonant impedance sensor with sensor data processed using principal component analysis (PCA) and displayed as a two-dimensional PCA scores plot. The five clusters of the ions (1-5 were formed in the scores plot of the PCA labeled as 1-5. FIG. 12C illustrates detection of the five different types of ions (1-5) displayed as three-dimensional PCA scores plot.

Figure 12D:
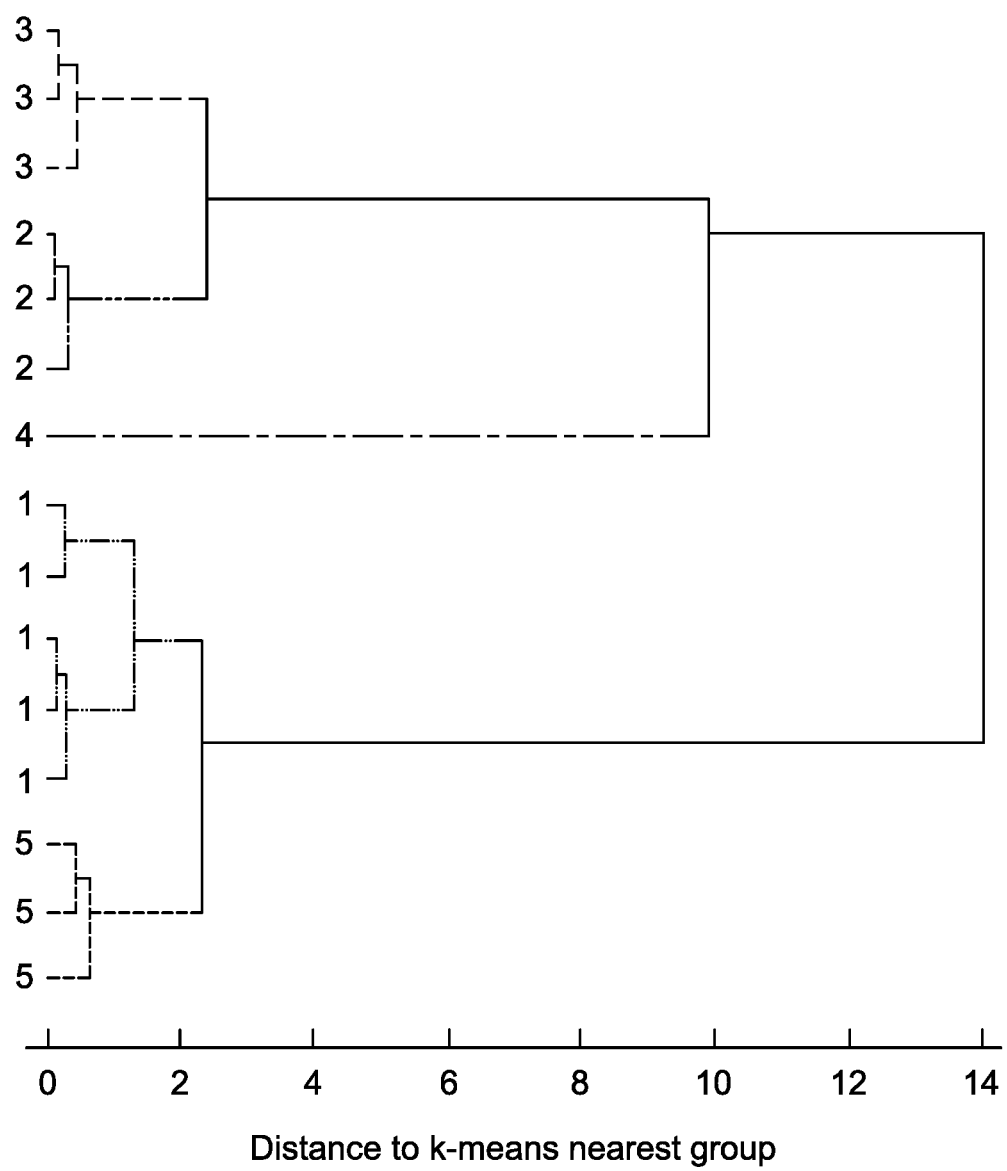
FIG. 12D illustrates an example of detection of five different types of ions in aqueous samples using plural outputs from a multivariable sensor with sensor data processed using hierarchical cluster analysis.

FIG. 12D illustrates analysis of the response of the multivariable resonant impedance sensor for detection of the five different types of ions (1-5) in aqueous samples with sensor data processed using hierarchical cluster analysis. Accordingly, a single multivariable sensor was able to discriminate five types of ions (1-5) by using a bare electrode structure without a sensing film.

In one embodiment, a subject may use a physiological sensor without revealing the identity of the subject, however the subject may have all or some of the benefits of having the physiological sensor in operational contact with the subject. Such exemplary scenarios can be industrial, educational, law-enforcement, entertainment, security, safety, military, or any other workers or other users. To avoid the need to store personal information and/or require a personal identified for an individual, upon first donning the sensor, and/or at given periodic intervals, a personalized baselining may be used. Alternatively, a personalized baselining may also be used before the intended use of the sensor. For example, the wearer may be asked to perform a set of tasks, for example a breath hold, a step test, or the like. The sensor and controller can track the response during and/or after each task to create a personalized baselining for the given wearer without the need to store personal information and/or to require a personal identifier for an individual.

The baselining data may be used, in an anonymous or unidentifiable manner, to correlate results from one user or from multiple different users without revealing the identify of the subject. In a non-limiting example, the results from the personal baselining could be compared to a database of results and used to customize alarm or event thresholds for the physiological and/or environmental sensors. In another non-limiting example, it may be discovered that individuals unable to hold their breath for a predetermined amount of time (e.g., 30 seconds, or the like) may require lower alarm levels for environmental carbon monoxide (CO) and/or carbon dioxide ($CO_2$), or other gases, as such, relative to individuals that are able to hold their breath for the predetermined amount of time. Should the personal baselining show the wearer falls into such a category, alarm levels and/or exposure durations could be changed accordingly. Said database could also contain a time history of events and/or alarms from previous users and could be used to predict potential alarm or even situations.

In one or more embodiments of the subject matter described herein, a sensor system includes a first sensor configured to detect one or more environmental conditions of an environment in operational contact with a subject, a second sensor configured to detect one or more physiological parameters of the subject in operational contact with an asset, and a control unit comprising one or more processors communicatively coupled with the first sensor and the second sensor. The one or more processors are configured to receive a first signal from the first sensor indicative of the one or more environmental conditions, and receive a second signal from the second sensor indicative of the one or more physiological parameters of the subject. The one or more processors are configured to determine a relation between the one or more environmental conditions from the first sensor and the one or more physiological parameters from the second sensor based on the first signal and the second signal. The one or more processors are configured to determine a responsive action of the asset based on one or more of the first signal indicative of the one or more environmental conditions of the environment in operational contact with the subject or the second signal indicative of the one or more physiological parameters of the subject in operational contact with the asset.

In one or more embodiments of the subject matter described herein, a sensor system includes a first sensor configured to detect one or more environmental conditions of an environment in operational contact with a subject, a second sensor configured to detect one or more physiological parameters of the subject in operational contact with an asset, and a control unit having one or more processors communicatively coupled with the first sensor and the second sensor. The one or more processors are configured to receive a first signal from the first sensor indicative of the one or more environmental conditions, and receive a second signal from the second sensor indicative of the one or more physiological parameters of the subject. The one or more processors are configured to determine a relation between the one or more environmental conditions from the first sensor and the one or more physiological parameters from the second sensor based on the first signal and the second signal. The one or more processors are configured to determine a responsive action of the subject based on the one or more of the first signal indicative of the one or more environmental conditions of the environment in operational contact with the subject or the second signal indicative of the one or more physiological parameters of the subject in operational contact with the asset. The one or more processors are configured to determine a responsive action of the asset based on the second signal indicative of the one or more physiological parameters of the subject.

Optionally, the first sensor is an environmental sensor configured to detect the one or more environmental conditions of the environment in operational contact with the subject.

Optionally, the first sensor is an environmental sensor configured to detect the one or more environmental conditions of the environment in operational contact with the subject with different detection resolutions.

Optionally, the second sensor is a physiological sensor configured to detect the one or more physiological parameters of the subject.

Optionally, the second sensor is a physiological sensor configured to detect the one or more physiological parameters of the subject with different detection resolutions.

Optionally, the first sensor is transferable between a first position and a second position.

Optionally, the second sensor is transferable between a first position and a second position.

Optionally, one or more of the first sensor or the second sensor is a wearable sensor.

Optionally, the sensor system also includes a weather center communicatively coupled with the control unit. The control unit is configured to obtain one or more ambient parameters of the weather center.

Optionally, the control unit is configured to determine a relation between the one or more environmental conditions, the one or more physiological parameters, and the one or more ambient parameters.

Optionally, the first sensor is a multivariable environmental sensor or a univariable environmental sensor.

Optionally, the second sensor is a multivariable physiological sensor or a univariable physiological sensor.

Optionally, the control unit includes a memory configured to store the first signal from the first sensor indicative of the one or more environmental conditions and store the second signal from the second sensor indicative of the one or more physiological parameters.

Optionally, the control unit is configured to transmit an output signal representative of the responsive action of the subject.

Optionally, the control unit is configured to transmit a notification to one or more of the subject or one or more users of the sensor system based on one or more of the first signal or the second signal exceeding a designated threshold.

Optionally, the one or more environmental conditions include one or more of at least one analyte of interest, particle matter contaminants, ultraviolet radiation exposure, ambient temperature, ambient atmospheric pressure, ambient relative humidity, or sensor acceleration.

Optionally, the one or more physiological parameters include one or more of skin temperature, body temperature, core body temperature, skin conductivity, blood pressure, blood glucose, respiration rate, oxygen rate, oxygen saturation, heart rate, heart sounds, or body movement.

Optionally, the one or more physiological parameters are parameters related to one or more of neural, respiratory, circulatory, cardiac, hemodynamic, or metabolic physiological functions.

Optionally, one or more of the first sensor or the second sensor is configured to change between an active mode and a stand-by mode. In the active mode, the one or more of the first sensor or the second sensor is configured to detect the one or more environmental conditions or the one or more physiological parameters, respectively. In the stand-by mode, the one or more of the first sensor or the second sensor are not configured to detect the one or more environmental conditions or the one or more physiological parameters, respectively.

Optionally, the one or more processors are configured to control one or more operational settings of the asset based on the second signal indicative of the one or more physiological parameters of the subject.

Optionally, the one or more of the first sensor or the second sensor is configured to change between a relatively-high-sensitivity mode and a relative-low-sensitivity mode.

In one or more embodiments of the subject matter described herein, a method includes detecting one or more environmental conditions of an environment in operational contact with a subject with a first sensor of a sensor system, and detecting one or more physiological parameters of the subject in operational contact with an asset with a second sensor of the sensor system. A first signal is received from the first sensor indicative of the one or more environmental conditions of the environment in operational contact with the subject. A second signal is received from the second sensor indicative of the one or more physiological parameters of the subject. A relation is determined between the one or more environmental conditions from the first sensor and the one or more physiological parameters from the second sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset is determined based on the second signal indicative of the one or more physiological parameters of the subject.

Optionally, the first sensor is an environmental sensor configured to detect the one or more environmental conditions of the environment in operational contact with the subject.

Optionally, the second sensor is a physiological sensor configured to detect the one or more physiological parameters of the subject.

Optionally, the first sensor is transferable between a first position and a second position.

Optionally, the second sensor is transferable between a first position and a second position.

Optionally, one or more of the first sensor or the second sensor is a wearable sensor.

Optionally, the method also includes obtaining one or more ambient parameters.

Optionally, the method also includes determining a relation between the one or more environmental conditions, the one or more physiological parameters, and the one or more ambient parameters.

Optionally, the method also includes storing the first signal from the first sensor indicative of the one or more environmental conditions and storing the second signal from the second sensor indicative of the one or more physiological parameters.

Optionally, the method also includes transmitting an output signal representative of the responsive action of the subject.

Optionally, the method also includes transmitting a notification to one or more of the subject or one or more users of the sensor system based on one or more of the first signal or the second signal exceeding a designated threshold.

Optionally, the one or more environmental conditions include one or more of at least one analyte of interest, particle matter contaminants, ultraviolet radiation exposure, ambient temperature, ambient atmospheric pressure, ambient relative humidity, or sensor acceleration.

Optionally, the one or more physiological parameters include one or more of skin temperature, body temperature, core body temperature, skin conductivity, blood pressure, blood glucose, respiration rate, oxygen saturation, heart rate, heart sounds, or body movement.

Optionally, the one or more physiological parameters are parameters related to one or more of neural, respiratory, circulatory, cardiac, hemodynamic, or metabolic physiological functions.

Optionally, the method also includes changing one or more of the first sensor or the second sensor between an active mode and a stand-by mode. In the active mode, the one or more of the first sensor or the second sensor is configured to detect the one or more environmental conditions or the one or more physiological parameters, respectively. In the stand-by mode, the one or more of the first sensor or the second sensor is not configured to detect the one or more environmental conditions or the one or more physiological parameters.

Optionally, the method also includes controlling one or more operational settings of the asset based on the second signal indicative of the one or more physiological parameters of the subject.

In one or more embodiments of the subject matter described herein, a method includes detecting one or more environmental conditions of an environment in operational contact with a subject with an environmental sensor of a sensor system, and detecting one or more physiological parameters of the subject in operational contact with an asset with a physiological sensor of the sensor system. A first signal is received from the environmental sensor indicative of the one or more environmental conditions of the environment in operational contact with the subject. A second signal is received from the physiological sensor indicative of the one or more physiological parameters of the subject. A relation is determined between the one or more environmental conditions from the environmental sensor and the one or more physiological parameters from the physiological sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset of the subject is determined based on the second signal indicative of the one or more physiological parameters of the subject. A notification is transmitted to one or more of the subject or one or more users of the sensor system based on one or more of the environmental signal or the physiological signal exceeding a designated threshold.

In one or more embodiments of the subject matter described herein, a method includes detecting one or more environmental conditions of an environment in operational contact with a subject with a first sensor of a sensor system, detecting one or more physiological parameters of the subject in operational contact with an asset with a second sensor of the sensor system, and communicatively coupling the first sensor and the second sensor with a control unit. A first signal is received from the first sensor indicative of the one or more environmental conditions of the environment in operational contact with the subject. A second signal is received from the second sensor indicative of the one or more physiological parameters of the subject. A relation is determined between the one or more environmental conditions from the first sensor and the one or more physiological parameters from the second sensor based on the first signal and the second signal. A responsive action of the subject is determined based on one or more of the first signal indicative of the one or more environmental conditions of the environment in operational contact with the subject or the second signal indicative of the one or more physiological parameters of the subject. A responsive action of the asset is determined based on the second signal indicative of the one or more physiological parameters of the subject.

Optionally, the method also includes creating a multi-dimensional assessment score from one or more contextual factors based on the relation between the one or more environmental conditions from the first sensor and the one or more physiological parameters from the second sensor.

Optionally, the multi-dimensional assessment score is one or more of a numerical indicator or a color-coded value within a range of colors.

Optionally, the method also includes communicating the multi-dimensional assessment score across a network of one or more of the subject or the asset.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled," "operationally contacted," "operational contact" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A sensor system comprising:
a first sensor configured to detect one or more environmental conditions of an environment in operational contact with a subject;
a second sensor configured to detect one or more physiological parameters of the subject in operational contact with an asset; and
a control unit comprising one or more processors communicatively coupled with the first sensor and the second sensor,
wherein the one or more processors are configured to receive a first signal from the first sensor indicative of the one or more environmental conditions,
wherein the one or more processors are configured to receive a second signal from the second sensor indicative of the one or more physiological parameters of the subject,
wherein at least one of the first or the second sensors are configured to change between an active mode and a stand-by mode, wherein in the active mode the at least one of the first or second sensors are configured to detect the one or more environmental conditions or the one or more physiological parameters, respectively, and in the stand-by mode, the at least one of the first or second sensors are not configured to detect the one or more environmental conditions or the one or more physiological parameters, respectively,
wherein the one or more processors are configured to determine a relation between the one or more environmental conditions from the first sensor and the one or more physiological parameters from the second sensor based on the first signal and the second signal, and
wherein the one or more processors are configured to determine a responsive action of the asset based on one or more of the first signal indicative of the one or more environmental conditions of the environment in operational contact with the subject or the second signal indicative of the one or more physiological parameters of the subject in operational contact with the asset.

2. The sensor system of claim 1, wherein the one or more processors are configured to determine a responsive action of the subject based on one or more of the first signal indicative of the one or more environmental conditions of the environment in operational contact with the subject or the second signal indicative of the one or more physiological parameters of the subject in operational contact with the asset.

3. The sensor system of claim 1, wherein the first sensor is an environmental sensor configured to detect the one or more environmental conditions of the environment in operational contact with the subject.

4. The sensor system of claim 1, wherein the second sensor is a physiological sensor configured to detect the one or more physiological parameters of the subject.

5. The sensor system of claim 1, wherein one or more of the first sensor or the second sensor is transferable between a first position and a second position.

6. The sensor system of claim 1, wherein one or more of the first sensor or the second sensor is a wearable sensor.

7. The sensor system of claim 1, further comprising a weather center communicatively coupled with the control unit, wherein the control unit is configured to obtain one or more ambient parameters from the weather center.

8. The sensor system of claim 7, wherein the control unit is configured to determine a relation between the one or more environmental conditions, the one or more physiological parameters, and the one or more ambient parameters.

9. The sensor system of claim 1, wherein the control unit comprises a memory configured to store the first signal from the first sensor indicative of the one or more environmental conditions and store the second signal from the second sensor indicative of the one or more physiological parameters.

10. The sensor system of claim 1, wherein the control unit is configured to transmit an output signal representative of the responsive action of the asset.

11. The sensor system of claim 1, wherein the control unit is configured to transmit a notification to one or more of the subject or one or more users of the sensor system based on one or more of the first signal or the second signal exceeding a designated threshold.

12. The sensor system of claim 1, wherein the one or more environmental conditions include one or more of at least one analyte of interest, particle matter contaminants, ultraviolet radiation exposure, ambient temperature, ambient atmospheric pressure, ambient relative humidity, or sensor acceleration.

13. The sensor system of claim 1, wherein the one or more physiological parameters include one or more of skin temperature, body temperature, core body temperature, skin conductivity, blood pressure, blood glucose, respiration rate, oxygen saturation, heart rate, heart sounds, or body movement.

14. The sensor system of claim 1, wherein the one or more physiological parameters are parameters related to one or more of neural, respiratory, circulatory, cardiac, hemodynamic, or metabolic physiological functions.

15. The sensor system of claim 1, wherein the one or more processors are configured to control one or more operational settings of the asset based on the second signal indicative of the one or more physiological parameters of the subject.

16. The sensor system of claim 1, wherein one or more of the first sensor or the second sensor is configured to change between a relatively-high-sensitivity mode and a relatively-low-sensitivity mode.

17. A method comprising:
detecting one or more environmental conditions of an environment in operational contact with a subject with a first sensor of a sensor system;
detecting one or more physiological parameters of the subject in operational contact with an asset with a second sensor of the sensor system;
receiving a first signal from the first sensor indicative of the one or more environmental conditions of the environment in operational contact with the subject;
receiving a second signal from the second sensor indicative of the one or more physiological parameters of the subject;
determining a relation between the one or more environmental conditions from the first sensor and the one or more physiological parameters from the second sensor based on the first signal and the second signal;
determining a responsive action of the subject based on one or more of the first signal indicative of the one or more environmental conditions of the environment in operational contact with the subject or the second signal indicative of the one or more physiological parameters of the subject;

determining a responsive action of the asset based on the second signal indicative of the one or more physiological parameters of the subject in operational contact with the asset; and changing at least one of the first or the second sensors between an active mode and a stand-by mode, wherein in the active mode the at least one of the first or second sensors are configured to detect the one or more environmental conditions or the one or more physiological parameters, respectively, and in the stand-by mode, the at least one of the first or second sensors are not configured to detect the one or more environmental conditions or the one or more physiological parameters, respectively.

18. The method of claim 17, wherein one or more of the first sensor or the second sensor is transferable between a first position and a second position.

19. The method of claim 17, wherein one or more of the first sensor or the second sensor is a wearable sensor.

20. The method of claim 17, further comprising obtaining one or more ambient parameters.

21. The method of claim 20, further comprising determining a relation between the one or more environmental conditions, the one or more physiological parameters, and the one or more ambient parameters.

22. The method of claim 17, further comprising storing the first signal from the first sensor indicative of the one or more environmental conditions and storing the second signal from the second sensor indicative of the one or more physiological parameters.

23. The method of claim 17, further comprising transmitting an output signal representative of the responsive action of the subject.

24. The method of claim 17, further comprising transmitting a notification to one or more of the subject or one or more users of the sensor system based on one or more of the first signal or the second signal exceeding a designated threshold.

25. The method of claim 17, further comprising controlling one or more operational settings of the asset based on the second signal indicative of the one or more physiological parameters of the subject.

26. The method of claim 17, further comprising transmitting a notification to one or more of the subject or one or more users of the sensor system based on one or more of the environmental signal or the physiological signal exceeding a designated threshold.

27. A method comprising:
detecting one or more environmental conditions of an environment in operational contact with a subject with a first sensor;

detecting one or more physiological parameters of the subject in operational contact with an asset with a second sensor, the asset being one or more of a vehicle system, an industrial system, or a medical device;

communicatively coupling the first sensor and the second sensor with a control unit;

receiving a first signal from the first sensor indicative of the one or more environmental conditions;

receiving a second signal from the second sensor indicative of the one or more physiological parameters of the subject;

determining a relation between the one or more environmental conditions from the first sensor and the one or more physiological parameters from the second sensor based on the first signal and the second signal;

determining a responsive action of the asset based on one or more of the first signal indicative of the one or more environmental conditions of the environment in operational contact with the subject or the second signal indicative of the one or more physiological parameters of the subject in operational contact with the asset; and changing at least one of the first or the second sensors between an active mode and a stand-by mode, wherein in the active mode the at least one of the first or second sensors are configured to detect the one or more environmental conditions or the one or more physiological parameters, respectively, and in the stand-by mode, the at least one of the first or second sensors are not configured to detect the one or more environmental conditions or the one or more physiological parameters, respectively.

28. The method of claim 27, further comprising creating a multi-dimensional assessment score from one or more contextual factors based on the relation between the one or more environmental conditions from the first sensor and the one or more physiological parameters from the second sensor.

29. The method of claim 28, wherein the multi-dimensional assessment score is one or more of a numerical indicator or a color-coded value within a range of colors.

30. The method of claim 28, further comprising communicating the multi-dimensional assessment score across a network of one or more of the subject or the asset.

* * * * *